(12) United States Patent
Pinsonneault, Sr. et al.

(10) Patent No.: US 10,430,555 B1
(45) Date of Patent: Oct. 1, 2019

(54) SYSTEMS AND METHODS FOR DETERMINING AND COMMUNICATING INFORMATION TO A PHARMACY INDICATING PATIENT ELIGIBILITY FOR AN INTERVENTION SERVICE

(71) Applicant: McKesson Corporation, San Francisco, CA (US)

(72) Inventors: Roger G. Pinsonneault, Sr., Alpharetta, GA (US); Scott Burgett, Sandy Springs, GA (US)

(73) Assignee: MCKESSON CORPORATION, San Francisco, CA (US)

( * ) Notice: Subject to any disclaimer, the term of this patent is extended or adjusted under 35 U.S.C. 154(b) by 448 days.

(21) Appl. No.: 14/209,248

(22) Filed: Mar. 13, 2014

(51) Int. Cl.
*G06F 19/00* (2018.01)

(52) U.S. Cl.
CPC .................. *G06F 19/3456* (2013.01)

(58) Field of Classification Search
None
See application file for complete search history.

(56) References Cited

U.S. PATENT DOCUMENTS

| | | | |
|---|---|---|---|
| 5,235,702 A | 8/1993 | Miller | |
| 5,244,556 A | 9/1993 | Inoue | |
| 5,359,509 A * | 10/1994 | Little | G06F 19/322 705/2 |
| 5,544,044 A | 8/1996 | Leatherman | |

(Continued)

FOREIGN PATENT DOCUMENTS

| | | |
|---|---|---|
| CA | 2482370 | 3/2006 |
| WO | WO 1995/003569 | 2/1995 |

(Continued)

OTHER PUBLICATIONS

HealthWatch Technology—HWT Inc. Website obtained from Mar. 25, 2002 web.archive.org.

(Continued)

*Primary Examiner* — Elaine Gort
*Assistant Examiner* — Rachelle L Reichert
(74) *Attorney, Agent, or Firm* — Alston & Bird LLP

(57) ABSTRACT

Systems and methods are provided for determining and communicating intervention service opportunities, such as medication therapy management services, that may be available for a patient, as part of processing a healthcare claim transaction. A healthcare claim transaction, such as a prescription benefit request transaction, may be received by the service provider computer from a healthcare provider computer. The service provider computer may determine if an intervention service is available for the patient and if an available intervention service notification has been transmitted to the pharmacy computer prior to the service provider computer receiving the healthcare claim transaction. The service provider computer may receive an approved adjudicated response and generate a patient intervention service form corresponding to the available intervention service for the patient. The service provider computer may transmit the patient intervention service form to the pharmacy computer and receive a completed patient intervention service form from the pharmacy computer.

20 Claims, 11 Drawing Sheets

(56) References Cited

U.S. PATENT DOCUMENTS

| | | | |
|---|---|---|---|
| 5,550,734 A * | 8/1996 | Tarter | G06Q 10/10 705/2 |
| 5,578,003 A | 11/1996 | Borger | |
| 5,628,530 A | 5/1997 | Thornton | |
| 5,644,778 A | 7/1997 | Burks et al. | |
| 5,704,044 A | 12/1997 | Tarter et al. | |
| 5,832,447 A | 11/1998 | Rieker et al. | |
| 5,950,169 A | 9/1999 | Borghesi et al. | |
| 6,006,242 A | 12/1999 | Poole et al. | |
| 6,012,035 A | 1/2000 | Freeman, Jr. et al. | |
| 6,073,104 A | 6/2000 | Field | |
| 6,081,786 A | 6/2000 | Barry et al. | |
| 6,202,923 B1 | 3/2001 | Boyer et al. | |
| 6,208,973 B1 | 3/2001 | Boyer et al. | |
| 6,324,516 B1 | 11/2001 | Shults et al. | |
| 6,330,546 B1 | 12/2001 | Gopinathan et al. | |
| 6,341,265 B1 | 1/2002 | Provost et al. | |
| 6,343,271 B1 | 1/2002 | Peterson et al. | |
| 6,578,003 B1 * | 6/2003 | Camarda | B82Y 10/00 705/2 |
| 6,632,251 B1 | 10/2003 | Rutten et al. | |
| 6,650,964 B2 | 11/2003 | Spano et al. | |
| 6,671,692 B1 | 12/2003 | Marpe et al. | |
| 6,671,693 B1 | 12/2003 | Marpe et al. | |
| 6,714,918 B2 | 3/2004 | Hillmer et al. | |
| 6,757,898 B1 | 6/2004 | Ilsen et al. | |
| 6,769,228 B1 | 8/2004 | Mahar | |
| 7,155,397 B2 | 12/2006 | Alexander et al. | |
| 7,720,697 B1 * | 5/2010 | Silverstein | G06F 19/328 705/3 |
| 8,036,913 B1 * | 10/2011 | Pinsonneault | G06F 19/328 705/2 |
| 8,046,242 B1 | 10/2011 | daCosta | |
| 8,060,379 B1 * | 11/2011 | Pinsonneault | G06Q 30/06 705/2 |
| 8,099,339 B1 | 1/2012 | Pinsonneault | |
| 8,244,556 B1 * | 8/2012 | Ringold | G06Q 10/10 705/2 |
| 8,335,672 B1 * | 12/2012 | Ringold | G06Q 50/24 703/2 |
| 8,386,274 B1 * | 2/2013 | Pinsonneault | G06Q 50/24 705/2 |
| 8,386,276 B1 | 2/2013 | Liu et al. | |
| 8,392,209 B1 * | 3/2013 | Bertha | G06F 19/328 705/2 |
| 8,392,219 B1 * | 3/2013 | Pinsonneault | G06Q 50/22 705/2 |
| 8,688,468 B1 | 4/2014 | daCosta et al. | |
| 8,725,532 B1 | 5/2014 | Ringold | |
| 8,768,724 B2 | 7/2014 | Whiddon et al. | |
| 9,122,783 B2 | 9/2015 | Carson et al. | |
| 9,443,370 B2 | 9/2016 | Carson et al. | |
| 2001/0041993 A1 | 11/2001 | Campbell | |
| 2001/0047281 A1 | 11/2001 | Keresman | |
| 2002/0002495 A1 | 1/2002 | Ullman | |
| 2002/0029157 A1 | 3/2002 | Marchosky | |
| 2002/0035488 A1 | 3/2002 | Aquila et al. | |
| 2002/0046169 A1 | 4/2002 | Keresman et al. | |
| 2002/0049617 A1 | 4/2002 | Lencki et al. | |
| 2002/0055856 A1 | 5/2002 | Adams | |
| 2002/0065687 A1 | 5/2002 | Onoue | |
| 2002/0087583 A1 | 7/2002 | Morgan et al. | |
| 2002/0111832 A1 | 8/2002 | Judge | |
| 2002/0120559 A1 | 8/2002 | O'Mara et al. | |
| 2002/0133503 A1 | 9/2002 | Amar et al. | |
| 2002/0138155 A1 | 9/2002 | Bristol | |
| 2002/0143434 A1 | 10/2002 | Greeven et al. | |
| 2002/0198831 A1 | 12/2002 | Patricelli et al. | |
| 2003/0009367 A1 | 1/2003 | Morrison | |
| 2003/0050799 A1 | 3/2003 | Jay et al. | |
| 2003/0050803 A1 | 3/2003 | Marchosky | |
| 2003/0069020 A1 | 4/2003 | Hillmer et al. | |
| 2003/0074225 A1 * | 4/2003 | Borsand | G06F 19/328 705/3 |
| 2003/0083903 A1 | 5/2003 | Myers | |
| 2003/0120588 A1 | 6/2003 | Dodd et al. | |
| 2003/0130868 A1 | 7/2003 | Coelho | |
| 2003/0149625 A1 | 8/2003 | Leonardi et al. | |
| 2003/0154163 A1 | 8/2003 | Phillips et al. | |
| 2003/0158755 A1 | 8/2003 | Neuman | |
| 2003/0229519 A1 | 12/2003 | Eidex et al. | |
| 2003/0229540 A1 | 12/2003 | Algiene | |
| 2004/0006490 A1 * | 1/2004 | Gingrich | G06F 19/328 705/2 |
| 2004/0039599 A1 | 2/2004 | Fralic | |
| 2004/0054685 A1 * | 3/2004 | Rahn | G06Q 40/02 |
| 2004/0064215 A1 | 4/2004 | Greeven et al. | |
| 2004/0073457 A1 | 4/2004 | Kalies | |
| 2004/0078234 A1 | 4/2004 | Tallal, Jr. | |
| 2004/0078247 A1 | 4/2004 | Rowe et al. | |
| 2004/0088187 A1 * | 5/2004 | Chudy | G06Q 10/10 705/2 |
| 2004/0093242 A1 | 5/2004 | Cadigan et al. | |
| 2004/0117205 A1 | 6/2004 | Reardan et al. | |
| 2004/0117323 A1 | 6/2004 | Mindala | |
| 2004/0133452 A1 | 7/2004 | Denny et al. | |
| 2004/0148198 A1 | 7/2004 | Kalies | |
| 2004/0178112 A1 | 9/2004 | Snyder | |
| 2004/0225528 A1 * | 11/2004 | Brock | G06F 19/3456 705/2 |
| 2004/0249745 A1 | 12/2004 | Baaren | |
| 2005/0015280 A1 | 1/2005 | Gabel et al. | |
| 2005/0060201 A1 | 1/2005 | Connely, III et al. | |
| 2005/0065821 A1 * | 3/2005 | Kalies, Jr. | G06Q 30/02 705/2 |
| 2005/0090425 A1 | 4/2005 | Reardan et al. | |
| 2005/0102169 A1 | 5/2005 | Wilson | |
| 2005/0137912 A1 * | 6/2005 | Rao | G06Q 10/10 705/4 |
| 2005/0154627 A1 | 7/2005 | Zuzek et al. | |
| 2005/0187791 A1 * | 8/2005 | DiMaggio | G06Q 50/22 705/2 |
| 2005/0187793 A1 | 8/2005 | Myles | |
| 2005/0197862 A1 | 9/2005 | Paterson et al. | |
| 2005/0209879 A1 | 9/2005 | Chalmers | |
| 2005/0240473 A1 | 10/2005 | Ayers, Jr. et al. | |
| 2005/0288972 A1 | 12/2005 | Marvin et al. | |
| 2006/0020514 A1 | 1/2006 | Yered | |
| 2006/0026041 A1 | 2/2006 | Ullman | |
| 2006/0062734 A1 | 3/2006 | Melker et al. | |
| 2006/0074717 A1 | 4/2006 | Feldman et al. | |
| 2006/0106648 A1 | 5/2006 | Esham et al. | |
| 2006/0129434 A1 | 6/2006 | Smitherman et al. | |
| 2006/0149784 A1 | 7/2006 | Tholl et al. | |
| 2006/0184391 A1 | 8/2006 | Barre et al. | |
| 2006/0217824 A1 | 9/2006 | Allmon | |
| 2006/0259363 A1 | 11/2006 | Jhetam et al. | |
| 2006/0266826 A1 * | 11/2006 | Banfield | G06F 19/3443 235/383 |
| 2007/0005402 A1 | 1/2007 | Kennedy et al. | |
| 2007/0050209 A1 | 3/2007 | Yered | |
| 2007/0050219 A1 | 3/2007 | Sohr | |
| 2007/0136100 A1 * | 6/2007 | Daugherty | G06Q 20/10 705/3 |
| 2007/0162303 A1 | 7/2007 | Wiley et al. | |
| 2007/0214009 A1 * | 9/2007 | Epstein | G06F 19/3443 705/2 |
| 2007/0233525 A1 | 10/2007 | Boyle | |
| 2007/0233526 A1 * | 10/2007 | Hoffman | G06F 19/328 705/4 |
| 2007/0239493 A1 | 10/2007 | Sweetland et al. | |
| 2007/0260491 A1 | 11/2007 | Palmer et al. | |
| 2007/0276697 A1 | 11/2007 | Wiley, II et al. | |
| 2008/0015893 A1 * | 1/2008 | Miller | G06F 19/3456 705/2 |
| 2008/0015894 A1 * | 1/2008 | Miller | G06F 19/3431 705/2 |
| 2008/0097784 A1 | 4/2008 | Miller et al. | |
| 2008/0112615 A1 | 5/2008 | Obrea | |
| 2008/0288281 A1 | 11/2008 | Shell et al. | |
| 2008/0312954 A1 | 12/2008 | Ullrich et al. | |

(56) References Cited

U.S. PATENT DOCUMENTS

| | | | |
|---|---|---|---|
| 2009/0048863 A1* | 2/2009 | Kozlowski | G06Q 50/22 705/2 |
| 2009/0144087 A1* | 6/2009 | Kelsch | G06Q 50/24 705/3 |
| 2009/0164376 A1* | 6/2009 | Guthrie | G06Q 50/22 705/50 |
| 2009/0281824 A1* | 11/2009 | Hardaway | G06Q 50/22 705/2 |
| 2009/0327363 A1* | 12/2009 | Cullen | G06F 19/3456 |
| 2010/0082367 A1* | 4/2010 | Hains | G06F 19/3456 705/2 |
| 2010/0305975 A1 | 12/2010 | Daya et al. | |
| 2010/0312576 A1* | 12/2010 | Brown | G06Q 10/10 705/2 |
| 2010/0324936 A1* | 12/2010 | Vishnubhatla | G06F 19/322 705/3 |
| 2011/0106556 A1* | 5/2011 | Patel | G06F 19/345 705/2 |
| 2011/0145018 A1* | 6/2011 | Fotsch | G06F 19/326 705/3 |
| 2011/0161109 A1* | 6/2011 | Pinsonneault | G06Q 50/22 705/3 |
| 2011/0173020 A1 | 7/2011 | Bailey et al. | |
| 2011/0282690 A1 | 11/2011 | Patel et al. | |
| 2011/0288886 A1 | 11/2011 | Whiddon et al. | |
| 2012/0046970 A1 | 2/2012 | Potts et al. | |
| 2012/0173263 A1* | 7/2012 | Nease, Jr. | G06Q 50/22 705/2 |
| 2012/0310661 A1 | 12/2012 | Greene | |
| 2013/0151373 A1 | 6/2013 | Flanagan | |
| 2013/0253700 A1 | 9/2013 | Carson et al. | |
| 2014/0025545 A1 | 1/2014 | Carson et al. | |
| 2014/0156298 A1* | 6/2014 | Crawford | G06F 19/3456 705/2 |
| 2014/0188498 A1 | 7/2014 | Petrimoulx et al. | |

FOREIGN PATENT DOCUMENTS

| | | |
|---|---|---|
| WO | WO 2000/039737 | 7/2000 |
| WO | 0173652 A1 | 10/2001 |
| WO | WO 2007/025295 | 3/2007 |

OTHER PUBLICATIONS

GAO publication GAO-01-662 "Medicaid: State Efforts to Control Improper Payments Vary" Jun. 2001.

Gregory J. Borca, "Technology Curtails Health Care Fraud" Managed Care Magazine, Apr. 2001.

McKesson & American Pharmacy Alliance Agree to Offer Omnlink Connectivity to Retail Pharmacies: More than 11,000 Pharmacies Gain Ability to Access Centralized Pharmacy Application. Bus. Wire. New York: Jul. 28, 1998 did=323992868&sid=4&Fmt=3 &clientId=19649&RQT&VNam=PQD>.

NDC Health Information Services Announces Contract with Arrow Pharmacy and Nutrition Centers for Pre & Post Editing Service. PR Newswire. New York: Mar. 11, 1999. p. 1. [Retr. Internet Oct. 30, 2007] URL: <http://proquest.umi.com/pqdweb?did=39644468&sid=4&Fmt=3&clientId=19649&RQT=309&VNam=PQD>.

Titus, Nancy Riaden. Health Insurance Industry Battles High Cost Fraud, Journal Record, Nov. 20, 1993, p. no page cite.

Sternberg et al., Using Cultural Algoritbyms too Support Re-engineering of Rule-Based Expert systems in Dynamic Performance Environments: A Case Study in Fraud Detection, IEEE Transactions on Evolutionary Computation, vol. 1 No. 4, Nov. 1997, pp. 225-243.

Stefano, Bordoni. Insurance Faud Evaluation a Fuzzy Expert System, 2001 IEEE International Fuzzy Systems Conference, pp. 1491-1494.

Radcliffe, J.G.Y., "The Insurance Industry's Use of Databases to Prevent and Detect Fraud, and Improve Recoveries", European Convention on Security and Detection, Conference Publication No. 408, May 16-18, 1995, pp. 216-224.

NDC Health Provides United Drugs With Intelligent Valued-Added Network Services and New Information Solutions. PR Newswire. New York: Dec. 12, 2000. p. 1. [Retr. Internet Apr. 11, 2007] URL: <http://proquest.umi.com/pqdweb?did=65133864&sid=4&Fmt=3 &clientId=19649&RQT=309&VNam=PQD>.

Pharmacy Industry Leaders Launch Firm to Supply Real-Time Data. PR Newswire. New York: Jul. 30, 2001. p. 1. [Retr. Internet Oct. 30, 2007] URL: <http://proquest.umi.com/pqdweb?did=77135077 &sid=4&Fmt=11&clientId=19649&RQT=309&VNam=PQD>.

Wholesalers Get Into Technology Game. Chain Drug Review. Feb. 15, 1999. p. Rx20 [Retr. From Internet Oct. 30, 2007] URL:<http://www.accessmylibrary.com/coms/summary_0286-487914_ITM>.

Glaser, M. Computer Eliminates Third-Party Administrator. Drug Topics. Oradell: May 3, 1993. vol. 137, Issu.9; p. 54, 3 pgs. [Retr. From Internet Apr. 11, 2007]. URL: <http://proquest.umi.com/pqdweb?did=779533&sid=5&Fmt=11&clientId=19649&RQT=309 &VNam=PQD>.

International Search Report for PCT/US2003/015982 dated Jun. 2, 2004.

International Search Report for PCT/US2003/015992 dated Jun. 2, 2004.

Non-final Office Action for U.S. Appl. No. 10/439,423 dated Jul. 31, 2008.

Final Office Action for U.S. Appl. No. 10/439,423 dated Dec. 9, 2008.

Non-final Office Action for U.S. Appl. No. 10/439,423 dated Apr. 28, 2009.

Final Office Action for U.S. Appl. No. 10/439,423 dated Dec. 24, 2009.

Non-final Office Action for U.S. Appl. No. 11/961,559 dated Mar. 3, 2010.

Final Office Action for U.S. Appl. No. 11/961,559 dated Nov. 10, 2010.

Non-final Office Action for U.S. Appl. No. 12/411,043 dated Feb. 8, 2011.

Non-final Office Action for U.S. Appl. No. 12/411,075 dated Jul. 7, 2011.

Final Office Action for U.S. Appl. No. 12/411,043 dated Jul. 7, 2011.

Non-Final Office Action for U.S. Appl. No. 12/480,907 dated Sep. 20, 2011.

Non-Final Office Action for U.S. Appl. No. 12/730,897 dated Sep. 29, 2011.

Final Office Action for U.S. Appl. No. 12/411,075 dated Oct. 26, 2011.

Office Action for Canadian Application No. 2,485,034 dated Nov. 22, 2011.

Non-Final Office Action for U.S. Appl. No. 12/820,750 dated Feb. 1, 2012.

Office Action for Canadian Application No. 2,485,031 dated Apr. 5, 2012.

Final Office Action for U.S. Appl. No. 12/480,907 dated May 4, 2012.

Final Office Action for U.S. Appl. No. 12/820,750 dated Jul. 6, 2012.

Non-Final Office Action for U.S. Appl. No. 12/480,907 dated Sep. 12, 2012.

Non-Final Office Action for U.S. Appl. No. 12/730,897 dated Nov. 8, 2012.

Final Office Action for U.S. Appl. No. 12/480,907 dated Apr. 2, 2013.

Non-Final Office Action for U.S. Appl. No. 12/411,075 dated May 22, 2013.

Final Office Action for U.S. Appl. No. 12/730,897 dated Nov. 22, 2013.

Notice of Allowance for U.S. Appl. No. 13/538,377 dated Dec. 27, 2013.

Non-Final Office Action for U.S. Appl. No. 13/566,693 dated Apr. 30, 2014.

Letter Restarting Period for Response for U.S. Appl. No. 13/566,693 dated Jul. 9, 2014.

Non-Final Office Action for U.S. Appl. No. 13/628,623 dated Sep. 25, 2014.

(56) References Cited

OTHER PUBLICATIONS

Final Office Action for U.S. Appl. No. 13/566,693 dated Nov. 6, 2014.
Non-Final Office Action for U.S. Appl. No. 13/735,212 dated Jan. 14, 2015.
Non-Final Office Action for U.S. Appl. No. 13/763,618 dated Jan. 15, 2015.
Final Office Action for U.S. Appl. No. 13/628,623 dated Mar. 11, 2015.
Final Office Action for U.S. Appl. No. 13/735,212 dated Jun. 12, 2015.
Non-final Office Action for U.S. Appl. No. 13/927,862 dated Jul. 6, 2015.
Non-final Office Action for U.S. Appl. No. 13/566,693 dated Jul. 23, 2015.
Non-final Office Action for U.S. Appl. No. 13/628,623 dated Dec. 18, 2015.
Final Office Action for U.S. Appl. No. 13/566,693 dated Dec. 23, 2015.
NPPES Registry Lookup Tool—https://web.archive.org/web/20130213231441/https://npiregistry.cms.hhs.gov/NPPESRegistry/NIPRegistryHome.do Date: Feb. 13, 2013.
NDC Code Directory Description—https://web.archive.org/web/20090603081835/http://www.fda.gov/Drugs/InformationOnDrugs/ucm142438.htm Jun. 3, 2009.
NDC Code Direcotry Tool—https://web.archive.org/web/20090327121011/http://www.accessdata.fda.gov/scripts/cder/ndc/default.cfm Date: Mar. 29, 2009.
Non-final Office Action for U.S. Appl. No. 14/062,593 dated Sep. 2, 2015.
Non-final Office Action for U.S. Appl. No. 13/763,618 dated Sep. 22, 2015.
Final Office Action for U.S. Appl. No. 13/763,618 dated Mar. 28, 2016.
Non-Final Office Action for U.S. Appl. No. 14/062,593 dated Jun. 3, 2016.
Final Office Action for U.S. Appl. No. 13/927,862 dated Sep. 22, 2016, 17 pages.
Final Office Action for U.S. Appl. No. 14/062,593 dated Nov. 4, 2016, 21 pages.
Final Office Action for U.S. Appl. No. 13/763,618 dated Apr. 28, 2017.
Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.
Anonymous, Medic; On-line Goes In-House, Chain Store Age Executive, Jan. 1987, vol. 63, Issue 1, USA; Abstract only.
Anonymous, Pharmacy Industry Leaders Launch Firm to Supply Real-Time Data. PR Newswire. Jul. 30, 2001, p. 1 New York, NY, USA.
Anonymous, TechRx Announces Successful Beta Deployment of T-Rex. PR Newswire. May 13, 2002.
Final Office Action for U.S. Appl. No. 13/628,623 dated Jun. 14, 2016.
Final Office Action for U.S. Appl. No. 14/209,248 dated Nov. 4, 2016, 35 pages.
Lamb, J., New Era of Electronic Medicine Management: E-Prescriptions, Britain's Traditionally Cautious National-Health Service is Starting Trials for Online Prescription, with the Aim of Cutting Costs. Financial Times, London, Feb. 21, 2001, p. 6, London, United Kingdom.
Non-Final Office Action for U.S. Appl. No. 14/209,248 dated Apr. 22, 2016.
Non-Final Office Action for U.S Appl. No. 13/763,618 dated Sep. 23, 2016, 21 pages.
Office Action for U.S. Appl. No. 14/062,593 dated Jun. 3, 2016.
Office Action for U.S. Appl. No. 14/062,593 dated May. 18, 2018.
Office Action for U.S. Appl. No. 14/062,593 dated Nov. 4, 2016.
Office Action for U.S. Appl. No. 14/062,593 dated Sep. 2, 2015.
Office Action for U.S. Appl. No. 14/062,593 dated Sep. 29, 2017.
Office Action for U.S. Appl. No. 14/519,626 dated Jan. 29, 2018.
Office Action for U.S. Appl. No, 14/519,626 dated May 1, 2017.
Office Action for U.S. Appl. No. 14/519,626 dated Oct. 31, 2018 .
Sampson, R.J., Taking Control of Health Care Costs, Best's Review—Life Health Insurance Edition, Nov. 1983, vol. 84, Issue 7, USA; Abstract only.
Office Action for U.S. Appl. No. 14/062,593 dated Jun. 6, 2019.
Office Action for U.S. Appl. No. 14/519,626 dated Jun. 3, 2019.

\* cited by examiner

SYSTEMS AND METHODS FOR DETERMINING AND COMMUNICATING INFORMATION TO A PHARMACY INDICATING PATIENT ELIGIBILITY FOR AN INTERVENTION SERVICE

TECHNICAL FIELD

Aspects of the disclosure relate generally to healthcare transactions and more particularly to systems and methods for determining and communicating services associated with an intervention, such as medication therapy management, that may be available for a patient, as part of the processing of a healthcare transaction.

BACKGROUND

An intervention is an effort to promote behaviors that optimize mental and physical health of the patient or discourage or reframe behaviors of the patient considered potentially health-averse. Medication therapy management (MTM) is medical care provided by pharmacists whose aim is to optimize drug therapy and improve therapeutic outcomes for patients. Medication therapy management includes a broad range of professional activities including, but not limited to, performing patient assessment and/or a comprehensive medication review, formulating a medication treatment plan, monitoring efficacy and safety of medication therapy, enhancing medication adherence through patient empowerment and education, and documenting and communicating MTM services to prescribers in order to maintain comprehensive patient care.

Medication therapy management includes five core components: a medication therapy review, personal medication record, medication-related action plan, intervention and/or referral, and documentation and follow-up. A medication therapy review is a systematic process of collecting patient and medication-related information which occurs during the pharmacist-patient encounter. In addition, the medication therapy review assists in the identification and prioritization of medication-related problems. During the medication therapy management encounter, the pharmacist develops a personal medication record for use by the patient. The personal medication record includes all prescription and non-prescription products/medications and may need to be updated periodically. After assessing and identifying medication-related problems, the pharmacist develops a patient-specific medication-related action plan. The medication-related action plan is a list of self-management actions necessary to achieve the patient's specific health goals. In addition, the patient and pharmacist utilize the medication-related action plan to record actions and track progress towards health goals. During the medication therapy management session, the pharmacist identifies medication-related problems and determines appropriate interventions for resolution. Following the patient encounter and/or intervention, the pharmacist must document his/her encounter and determine appropriate patient follow-up.

Providing pharmacies, pharmacy ownership, and service providers a systemized method for processing and tracking patient intervention information associated with an intervention, such as medication therapy management, can be a challenge with today's pharmacy computer systems. For example, it can be a challenge to notify a pharmacy, within the typical healthcare transaction processing, that a patient is eligible to receive a service, such as an intervention opportunity, associated with a fill and/or refill of a medication. Furthermore, should a pharmacy capture service information associated with a fill and/or refill of a medication, communication of the captured service information to the pharmacy ownership and or the service providers is typically delayed.

BRIEF DESCRIPTION OF THE DRAWINGS

Reference will now be made to the accompanying drawings, which are not necessarily drawn to scale, and wherein.

DETAILED DESCRIPTION OF EXEMPLARY EMBODIMENTS

Figure 1:
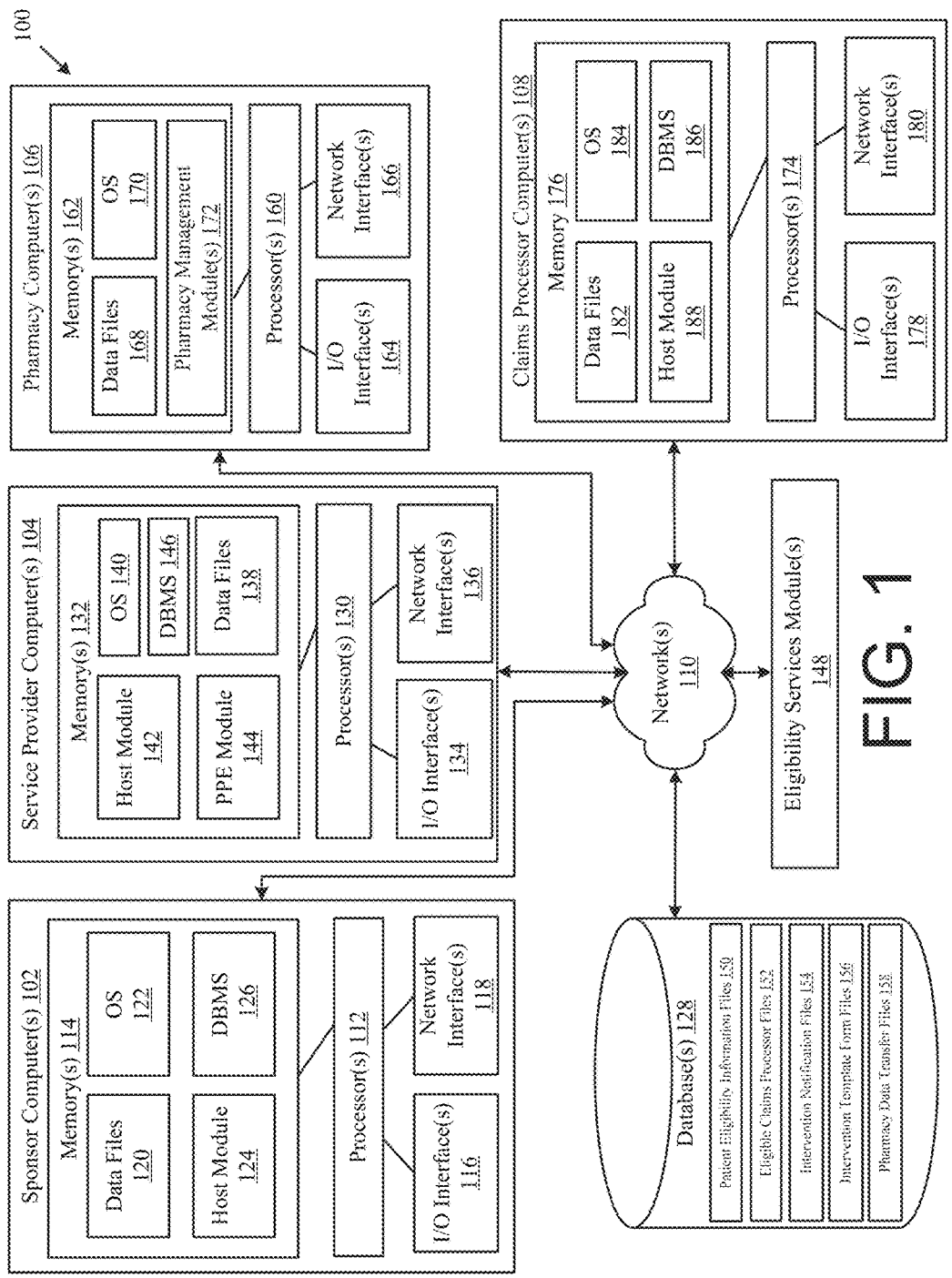
FIG. 1 illustrates an example system for facilitating, among other things, determining and communicating services associated with an intervention opportunity, such as a medication therapy management program, that may be available for a patient as part of the processing of a healthcare transaction, according to one exemplary embodiment.

Exemplary embodiments will now be described more fully hereinafter with reference to the accompanying drawings, in which exemplary embodiments are shown. The concepts disclosed herein may, however, be embodied in many different forms and should not be construed as limited to the exemplary embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Exemplary embodiments described herein include systems and methods for determining and communicating services associated with an intervention opportunity, such as a medication therapy management program that may be available for a patient as part of the processing of a healthcare transaction. In this regard, the available intervention service may be determined as a part of the processing of a healthcare transaction, such as a predetermination of benefits transaction, healthcare claim transaction, prescription claim or billing request, healthcare order transaction, or e-prescription transaction (i.e., electronic prescription order transaction, e-script, or e-prescription). In some example implementations, a prescription claim request may be communicated from a pharmacy computer to a service provider computer. In one example, the prescription claim request may be a National Council for Prescription Drug Programs (NCPDP) Telecommunication Standard formatted prescription claim request. The service provider computer may deliver the prescription claim request to a claims processor computer for adjudication. The service provider computer can receive an adjudicated response from the claims processor computer, which can include an indication of an approved (or paid) claim or a denied claim. If the adjudicated response indicates a paid or approved claim, the service provider computer can further generate a patient intervention service form for a medication or product and the patient identified in the prescription claim request. In certain example embodiments, the available intervention service may be determined from patient eligibility information accessed from a patient eligibility file. In one example, the patient intervention service form may be communicated to the pharmacy via an email correspondence. The patient intervention service form may be accessed by a pharmacist or other pharmacy employee in the pharmacy associated with the pharmacy computer during a prescription fill process. The patient intervention service form may be set aside for communication to the patient upon pick-up of the prescribed medication. In one example, a completed patient intervention service form may be communicated to the service provider computer from the pharmacy computer. The service provider computer may capture and facilitate storage of the intervention information in the patient intervention service form. The service provider computer may access the stored intervention information for the patient and generate an eligibility and services report including the accessed intervention information.

In one example, the service provider computer may employ an eligibility services module to determine whether an intervention service is available for the patient identified in the prescription claim request. The eligibility services module may access a patient eligibility file to determine whether a patient intervention service is available for the patient and/or medication identified in the prescription claim request. The eligibility services module may determine whether an intervention services notification has previously been sent to the pharmacy computer, communicating availability of the intervention service for the identified patient. If an intervention services notification has not been previously communicated for the patient, the eligibility services module may generate an intervention services notification to be communicated to the pharmacy computer along with a rejection response.

However, if an intervention services notification has previously been communicated to the pharmacy computer for the identified patient, and upon receipt of an approved adjudicated response, the eligibility services module may generate a patient intervention service form. The patient intervention service form may be populated with patient information included in the prescription claim request and/or the adjudicated response. The eligibility services module may access an email address for the pharmacy associated with the pharmacy computer, and communicate to the pharmacy computer, via the email address, the patient intervention service form.

The eligibility services module may also facilitate receipt of a completed patient intervention service form from the pharmacy computer. In one example, the completed patient intervention service form may be received by facsimile. The eligibility services module may generate an eligibility and intervention services report that may include information received in the completed patient intervention service form(s). The eligibility and intervention services report may be communicated to the pharmacy computer and a corporate computer associated with the pharmacy computer.

System Overview

FIGS. 1A and 1B illustrate an example system 100 for facilitating, among other things, determining and communicating intervention services associated with an intervention opportunity, such as a medication therapy management program, that may be available for a patient as part of the processing of a healthcare transaction. As shown in FIG. 1, the system 100 may include one or more sponsor computers 102, service provider computers 104, pharmacy computers 106, and/or claims processor computers 108. As desired, each of the sponsor computer 102, service provider computer 104, pharmacy computer 106, and/or claims processor computer 108 may include one or more processing devices that may be configured for accessing and reading associated computer-readable media having stored data thereon and/or computer-executable instructions for implementing various embodiments of the disclosure.

Generally, network devices and systems, including one or more sponsor computers 102, service provider computers 104, pharmacy computers 106, and/or claims processor computers 108, may include or otherwise be associated with suitable hardware and/or software for transmitting and receiving data and/or computer-executable instructions over one or more communication links or networks. These network devices and systems may also include any number of processors for processing data and executing computer-executable instructions, as well as other internal and peripheral components currently known in the art or which may be developed in the future. Further, these network devices and systems may include or be in communication with any number of suitable memory devices operable to store data and/or computer-executable instructions. By executing computer-executable instructions, each of the network devices may form a special-purpose computer or particular machine. As used herein, the term "computer-readable medium" describes any medium for storing computer-executable instructions.

As shown in FIG. 1, the one or more sponsor computers 102, service provider computers 104, pharmacy computers 106, and/or claims processor computers 108 may be in communication with each other via one or more networks, such as network 110, which may include one or more independent and/or shared private and/or public networks including the Internet or a publicly switched telephone network. In other example embodiments, one or more components of the system 100 may communicate via direct connections and/or communication links. Each of these components—the sponsor computer 102, service provider computer 104, pharmacy computer 106, claims processor computer 108, and the network 110—will now be discussed in further detail. Although the components are generally discussed as singular components, as may be implemented in various example embodiments, in alternative exemplary embodiments each component may include any number of suitable computers and/or other components.

With continued reference to FIG. 1, one or more sponsor computers 102 may be associated (e.g., located within) with one or more organizations responsible for contracting an eligibility service program. For example, the sponsor may be an entity that provides information for intervention services that may be available for patient(s). The sponsor computer 102 may communicate information associated with intervention services available for eligible patients to the service provider computer 104. A sponsor computer 102 may be any suitable processor-driven device that facilitates the processing of the communicated information associated with intervention services, such as MTM program services, available for eligible patients to create, store, and maintain any data associated with the communication. The sponsor computer 102 may be a computing device that includes any number of server computers, mainframe computers, networked computers, desktop computers, personal computers, mobile devices, smartphones, digital assistants, personal digital assistants, tablet devices, Internet appliances, application-specific integrated circuits, microcontrollers, minicomputers, and/or any other processor-based devices. In certain embodiments, the operations and/or control of the sponsor computer 102 may be distributed among several processing components. For example, the functionality associated with the sponsor computer 102 may be performed by one or more modules of the service provider computer 104 and/or the pharmacy computer 106.

In addition to including one or more processors 112, the sponsor computer 102 may further include one or more memory devices (or memory) 114, one or more input/output ("I/O") interfaces 116, and one or more network interfaces 118. The memory devices 114 may be any suitable memory devices, for example, caches, read-only memory devices, random access memory devices, magnetic storage devices, removable storage devices, etc. The memory devices 114 may store data, executable instructions, and/or various program modules utilized by the sponsor device 102, for example, data files 120, an operating system ("OS") 122, a host module 124, and a database management system (DBMS) 126 to facilitate management of data files 120 and other data stored in the memory device 114 and/or one or more databases 128. The OS 122 may be a suitable software module that controls the general operation of the sponsor device 102. The OS 122 may be any operating system known in the art or which may be developed in the future including, but not limited to, Microsoft Windows®, Apple OSX™, Apple iOS™, Google Android™, Linux, Unix, or a mainframe operating system.

The one or more I/O interfaces 116 may facilitate communication between the eligibility sponsor computers 102 and one or more input/output devices, for example, one or more user interface devices, such as a display, keypad, control panel, touch screen display, remote control, microphone, etc., that facilitate user interaction with the eligibility sponsor computers 102. For example, the one or more I/O interfaces 116 may facilitate entry of information associated with a patient by a sponsor employee. The one or more network interfaces 118 may facilitate connection of the eligibility sponsor computers 102 to one or more suitable networks, for example, the network 110 illustrated in FIG. 1. In this regard, the eligibility sponsor computers 102 may receive and/or communicate information to other network components of the system 100, such as the service provider computer 104.

With continued reference to FIG. 1, one or more service provider computers 104 may be associated with (e.g., located within or providing computing services for) a service provider. In certain exemplary embodiments, the service provider computer 104 may be a switch/router that routes healthcare transactions and/or other healthcare requests. For example, the service provider computer 104 may route healthcare transactions, such as a predetermination of benefits transaction, healthcare claim transaction, prescription claim or billing request, healthcare order transaction, or e-prescription transaction (i.e., electronic prescription order transaction, e-script, or e-prescription), communicated from the pharmacy computer 106 to a claims processor computer 108, such as a pharmacy benefits manager (PBM), a healthcare insurer, a Medicare payor, other governmental insurance payor, or other third-party insurance payor. The service provider computer 104 may include, but is not limited to, any suitable processor-driven device that is configured for receiving, processing, and fulfilling the healthcare transactions from the pharmacy computer 106 relating to prescription information including, but not limited to, medications, medication identifiers (e.g., medication name(s), National Drug Code(s) (NDC) codes, RxNorm medication identifiers), quantity of medication to be dispensed, patient identifier information (i.e., name, gender, date of birth, residence address). Any number of sponsor computers 102, pharmacy computers 106, and/or claims processor computers 108 may be in communication with the service provider computer 104 as desired in various example embodiments.

The service provider computer 104 may include any number of special-purpose computers or other particular machines, application-specific integrated circuits, microcontrollers, personal computers, minicomputers, mainframe computers, servers, networked computers, and/or other processor-driven devices. In certain embodiments, the operations of the service provider computer 104 may be controlled by computer-executed or computer-implemented instructions that are executed by one or more processors of the service provider computer 104 to form a special-purpose computer or other particular machine that is operable to facilitate the receipt, routing, and/or processing of healthcare requests or healthcare transactions. The one or more processors that control the operations of the service provider computer 104 may be incorporated into the service provider computer 104 and/or may be in communication with the service provider computer 104 via one or more suitable networks. In certain example embodiments, the operations and/or control of the service provider computer 104 may be distributed among several processing components.

Similar to the sponsor computer 102, the service provider computer 104 may include one or more processors 130, one or more memory devices 132, one or more input/output ("I/O") interfaces 134, and one or more network interfaces 136. The one or more memory devices 132 may be any suitable memory device, for example, caches, read-only memory devices, random access memory devices, magnetic storage devices, removable storage devices, etc. The one or more memory devices 132 may store data, executable instructions, and/or various program modules utilized by the service provider computer 104, for example, data files 138, an operating system ("OS") 140, a host module 142, a pre- and post-edit (PPE) module 144, and a database management system (DBMS) 146 to facilitate management of data files 138 and other data stored in the memory devices 132 and/or one or more databases 128. The OS 140 may be any operating system known in the art or which may be developed in the future including, but not limited to, Microsoft Windows®, Apple OSX™, Linux, Unix, Apple iOS™, Google Android™, or a mainframe operating system. The OS 140 may be a suitable software module that controls the general operation of the service provider computer 104 and/or that facilitates the execution of other software modules.

The PPE module 144 may be operable to perform one or more pre-edits on a received healthcare transaction, such as predetermination of benefits transactions, healthcare claim transactions, prescription claim or billing requests, healthcare order transactions, or e-prescription transactions (i.e., electronic prescription order transactions, e-scripts, or e-prescriptions), prior to routing or otherwise communicating the received healthcare transaction to a suitable claims processor computer 108 or another destination received of the transaction. Additionally, the PPE module 144 may be operable to perform one or more post-edits on an adjudicated response that is received from a claims processor computer 108 for a healthcare transaction prior to routing the adjudicated response to the pharmacy computer 106. A wide variety of different pre-edits and/or post edits may be performed as desired in various embodiments of the disclosure. In certain example embodiments, an eligibility services module 148 and its functions may be incorporated into the PPE 144 and/or may be in communication with the PPE module 144. Alternatively, the functions of the eligibility services module 148 may be, or be part of, a separate computer from the service provider computer 104. In one example embodiment, the functions of the eligibility services module 148 may be incorporated into the pharmacy computer 106 and operable with the service provider computer 104, such as in the form of an application programming interface.

An eligibility services module 148 or an eligibility services application may also be operative with the service provider computer 104. The eligibility services module 148 may include computer-executable instructions operable for facilitating the communication of one or more intervention services available for an eligible patient. For example, the eligibility services module 148 may facilitate receipt of patient eligibility files including, for example, one or more intervention services available for an eligible patient. The patient eligibility file may include, for example, patient identification information (i.e., a patient's first and/or last name, a patient's social security number, a patient's health insurance claim number (HICN), etc.), patient contact information, and/or eligible intervention services information. In one example, eligible intervention services information may include, without limitation, an eligibility group, an eligibility type, an eligibility initiation, and/or an eligibility termination. The eligibility services module 148 may facilitate storage of data included in the patient eligibility file in one or more suitable databases and/or data storage devices, such as database 128.

In operation, the eligibility services module 148 may receive information associated with a healthcare transaction, such as a prescription claim request and/or an adjudicated response. In addition, the eligibility services module 148 may be further operable to access and/or be in communication with the sponsor computer 102. In one example, the eligibility services module 148 may access and/or be in communication with the sponsor computer 102 to identify a patient eligibility file available for the healthcare transaction and/or the adjudicated response. The eligibility services module may utilize the patient eligibility file to determine one or more intervention forms for the corresponding healthcare transaction and/or the adjudicated response. The eligibility services module 148 may pre-populate the one or more intervention forms with information available from the healthcare transaction and/or adjudicated response. In addition, the eligibility services module 148 may be further operable to communicate a response to the pharmacy computer 106. The response, in one example, may also include the one or more pre-populated intervention forms.

In addition the eligibility services module 148 may be further operable to communicate a response to the pharmacy computer 106. In one example, the response may also include the one or more pre-populated intervention forms. In certain example embodiments the eligibility services module 148 may be further operable to receive communication from the pharmacy computer 106. In one example, the eligibility services module 148 may receive one or more intervention forms completed by a patient. For example, upon receipt of the response and the one or more intervention forms, a pharmacist or other pharmacy employee at the pharmacy associated with the pharmacy computer 106 may access the intervention forms and present the forms to a patient and/or patient caregiver at the time the prescription identified with the healthcare transaction is received by the patient and/or patient caregiver. The eligibility services module 148 may be further operable to facilitate storage of data, including the patient completed intervention forms, in one or more suitable databases and/or data storage devices, such as the database 128.

In certain example embodiments, the eligibility services module 148 and/or the service provider computer 104 may be operable to generate one or more invoices or reports for the communicated, pre-populated, intervention forms and/or the received patient-completed intervention forms. A wide variety of different types of invoices or reports may be generated as desired in various embodiments of the disclosure. Invoices or reports may be sorted or formatted utilizing a wide variety of different criteria, parameters, and/or techniques. Additionally, the eligibility services module 148 and/or the service provider computer 104 may communicate or direct the communication of generated invoices or reports to the pharmacy computer 106 and/or a pharmacy back-office computer for the corporate offices of a pharmacy or pharmacy chain that the pharmacy is a member of and/or one or more other components of the system.

A wide variety of different techniques and/or software programs may be utilized to format a generated invoice and/or report. For example, an invoice or report may be formatted as a comma-separated-value (CSV) file, as a spreadsheet file, as a word processor file, as a text file, etc. Additionally, a wide variety of different communication techniques may be utilized to communicate a report to the recipient, including but not limited to, electronic transaction requests, email, short message service messaging, other electronic communications, paper mail, etc. An invoice report may be pushed to a recipient by the eligibility services module 148 or another portion of the service provider computer 104, or alternatively pulled from the eligibility services module 148 by a recipient submitting a request for one or more invoices or reports. Additionally, in certain embodiments, a report may be made available for download from an appropriate website or server, such as a website hosted by the service provider computer 104.

According to an example embodiment, the data files 138 may store healthcare transaction records associated with communications received from various sponsor computers 102, and/or various pharmacy computers 106, and/or various claims processor computers 108. The data files 138 may also store any number of suitable routing tables that facilitate determining the destination of communications received from a sponsor computer 102, a pharmacy computer 106, and/or a claims processor computer 108.

In one or more example embodiments of the disclosure, the service provider computer 104 may include or otherwise be in communication with one or more suitable databases and/or data storage devices 128, which may include, but are not limited to, one or more patient eligibility information files 150, one or more eligible claims processor files 152, one or more intervention notification files 154, one or more intervention template forms files 156, and one or more pharmacy data transfer files 158.

The patient eligibility information files 150 may include, without limitation, information captured by sponsor computers 102 and delivered to the service provider computer 104. For example, the patient eligibility information files 150 may include patient data such as a patient identifier (e.g., patient social security number, a subset of the patient social security number, a health insurance claim number (HICN), cardholder ID, etc.), a patient name, a patient gender, a date of birth, an address, a phone number, and/or an email address. The patient eligibility information files 150 may also include eligibility information, for example, without limitation, an eligibility group, an eligibility type, an eligibility initiation, an eligibility termination, and the like.

The eligible claims processor files 152 may include, without limitation, one or more claims processor computers 108 for which a healthcare transaction was rejected by the eligibility services module 148 and/or the service provider computer 104 during the processing of a received healthcare transaction, as described herein. In one example implementation, the healthcare transaction may be rejected based upon one or more previously encountered billing matters, one or more issues with billing reversal requests, and the like. The eligible claims processor files 152 may include at least a benefits provider identifier (e.g., Banking Identification Number (BIN Number), BIN Number and Processor Control Number (PCN), and/or BIN Number and Group ID), a benefits provider name, and/or a date and time captured at the time the benefits provider identifier was stored in the eligible claims processor files 152.

The intervention notification files 154 may include, without limitation, one or more previously communicated intervention forms and/or one or more intervention notifications (e.g., "INTERVENTION OPPORTUNITY—RESUBMIT CLAIM, ACCESS PHARMACY EMAIL IF PAID RESPONSE FOLLOWS, PRINT PATIENT INTERVENTION FORM, ASSOCIATE WITH RX."). The intervention notification files 154 may be organized by an intervention notification ID that may be assigned by the eligibility services module 148, the service provider computer 104, and/or any other component of the service provider computer 104.

The intervention template forms files 156 may include, without limitation, one or more paper and/or electronic template intervention forms. For example, the one or more template intervention forms may be organized according to an intervention type identifier (e.g., XX), an intervention template (e.g., standardized information to be applied to each intervention type), a medication and/or product type, and the like.

The pharmacy data transfer files 158 may include, without limitation, pharmacy information, including, but not limited to, a pharmacy identifier (e.g., National Council for Prescription Drug Programs (NCPDP) Provider ID, National Provider ID (NPI), group ID, BIN Number, or the like), a pharmacy and/or pharmacy chain name, a pharmacy email address, a pharmacy fax number, a pharmacy phone number, and/or a pharmacy street address. The pharmacy data transfer files 158 may be communicated to the services provider computer 104 by the pharmacy computer 106 and/or back-office pharmacy corporate computer (not shown) associated with the pharmacy computer 106.

The service provider computer 104 may include additional program modules for performing other processing methods described herein. Those of ordinary skill in the art will appreciate that the service provider computer 104 may include alternate and/or additional components, hardware, or software without departing from the scope of the disclosure.

With continued reference to the service provider computer 104, the one or more I/O interfaces 134 may facilitate communication between the service provider computer 104 and one or more input/output devices, for example, one or more user interface devices, such as a display, keypad, control panel, touch screen display, remote control, microphone, etc., that facilitate user interaction with the service provider computer 104. The one or more network interfaces 136 may facilitate connection of the service provider computer 104 to one or more suitable networks, for example, the network 110 illustrated in FIG. 1. In this regard, the service provider computer 104 may communicate with other components of the system 100, such as the sponsor computer 102, the pharmacy computers 106, the claims processor computers 108 and the database 128.

With continued reference to FIG. 1, any number of pharmacy computers 106 may be associated with (e.g., located within or providing computing services for) any number of pharmacies and/or pharmacists. Each pharmacy computer 106 may be any suitable processor-driven device that facilitates generating, communicating, processing, and/or fulfilling healthcare transactions such as predetermination of benefits transactions, healthcare claim transactions, prescription claim or billing requests, healthcare order transactions, or e-prescription transactions (i.e., electronic prescription order transactions, e-scripts, or e-prescriptions) received from or transmitted to the service provider computer 104. For example, a pharmacy computer 106 may be a processor-driven device associated with (i.e., located within or otherwise providing computing services for) a pharmacy. As desired, the pharmacy computers 106 may include any number of special-purpose computers or other particular machines, application-specific integrated circuits, microcontrollers, personal computers, minicomputers, mainframe computers, servers, and the like. In certain example embodiments, the operations of the pharmacy computers 106 may be controlled by computer-executed or computer-implemented instructions that are executed by one or more processors associated with the pharmacy computer 106 to form a special-purpose computer or other particular machine that is operable to facilitate the receipt, generation, and/or fulfillment of healthcare transactions (e.g., predetermination of benefits transactions, healthcare claim transactions, prescription claim or billing requests, healthcare order transactions, or e-prescription transactions (i.e., electronic prescription order transactions, e-scripts, or e-prescriptions)). The one or more processors that control the operations of the pharmacy computer 106 may be incorporated into the pharmacy computer 106 and/or may be in communication with the pharmacy computer 106 via one or more suitable networks. In certain example embodiments, the operations and/or control of the pharmacy computer 106 may be distributed among several processing components.

Similar to other components of the system 100, each pharmacy computer 106 may include one or more processors 160, one or more memory devices 162, one or more I/O interfaces 164, and one or more network interfaces 166. The one or more memory devices 162 may be any suitable memory devices, for example, caches, read-only memory devices, random access memory devices, magnetic storage devices, removable memory devices, etc. The one or more memory devices 162 may store data, executable instructions, and/or various program modules utilized by the pharmacy computers 106, for example, data files 168, an OS 170, and a pharmacy management module 172. The data files 168 may include any suitable information that is utilized by the pharmacy computers 106. The OS 170 may be a suitable software module that controls the general operation of the pharmacy computer 106. The OS 170 may also facilitate the execution of other software modules by the one or more processors 160. The OS 170 may be any operating system known in the art or which may be developed in the future including, but not limited to, Microsoft Windows®, Apple OSX™ Linux, Unix, Apple iOS™, Google Android™, or a mainframe operating system.

The one or more I/O interfaces 164 may facilitate communication between the pharmacy computer 106 and one or more input/output devices, for example, one or more user interface devices, such as a display, keypad, control panel, touch screen display, remote control, microphone, etc., that facilitate user interaction with the pharmacy computers 106. The one or more network interfaces 166 may facilitate connection of the pharmacy computer 106 to one or more suitable networks, for example, the network 110 illustrated in FIG. 1. In this regard, the pharmacy computer 106 may receive healthcare transactions and/or other communications from the service provider computer 104 and the pharmacy computers 106 may communicate information associated with processing healthcare transactions and/or prescription transactions to the service provider computer 104.

The pharmacy management module 172 may be a software application(s), including a dedicated program, for fulfilling healthcare transaction orders, reading and/or updating medical records (e.g., prescription records), facilitating patient billing, etc., as well as interacting with the service provider computer 104. For example, a pharmacist or other pharmacy employee, may utilize the pharmacy management module 172 in filling a prescription, recording and/or updating a patient's medical prescription history, and billing, generating, preparing, and providing a healthcare transaction to the service provider computer 104. Furthermore, the pharmacy computer 106 may utilize the pharmacy management module 172 to retrieve or otherwise receive data, messages, or responses from the sponsor computer 102 and/or other components of the system 100.

With continued reference to FIG. 1, each of the claims processor computers 108 may be any suitable processor-driven device that facilitates receiving, processing (e.g., adjudicating), and/or responding to healthcare transactions received from the service provider computer 104. For example, the claims processor computer 108 may be a processor-driven device associated with (e.g., located within or otherwise providing computing services for) a claims processor (i.e., Pharmacy Benefits Manager (PBM), claims payor, healthcare insurance company, Medicare, Medicaid, or other government healthcare insurance payor, Medicare Part D provider, claims clearinghouse, etc.). As desired, the claims processor computer 108 may include any number of special purpose computers or other particular machines, application specific circuits, microcontrollers, personal computers, minicomputers, mainframe computers, servers, and the like. In certain embodiments, the operations of the claims processor computer 108 may be controlled by computer-executed or computer-implemented instructions that are executed by one or more processors associated with the claims processor computer 108 to form a special purpose computer or other particular machine that is operable to facilitate the receipt, processing, and/or responding to healthcare transactions received from the service provider computer 104. The one or more processors that control the operations of the claims processor computer 108 may be incorporated into the claims processor computer 108 and/or in communication with the claims processor computer 108 via one or more suitable networks. In certain example embodiments of the disclosure, the operation and/or control of the claims processor computer 108 may be distributed amongst several processing components. In an alternate embodiment, the functions of the claims processor computer 108 may be incorporated into the service provider computer 104.

Similar to other components of the system 100, the claims processor computer 108 may include one or more processors 174, one or more memory devices 176, one or more input/output (I/O) interfaces 178, and one or more network interfaces 180. The memory 176 may be any suitable memory devices, for example, caches, read only memory devices, random access memory devices, magnetic storage devices, removable memory devices, etc. The one or more memory devices 176 may store data, executable instructions, and/or various program modules utilized by the claims processor computer 108, for example, data files 182, an operating system (OS) 184, a database management module ("DBMS") 186, and a host module 188. The data files 182 may include any suitable information that is utilized by the claims processor computer 108 to process healthcare transactions, for example, patient profiles, patient insurance information, other information associated with a patient, information associated with a healthcare provider, claims processing rules, etc.

The OS 184 may be a suitable software module that controls the general operation of the claims processor computer 108. The OS 184 may also facilitate the execution of other software modules by the one or more processors 174, for example the DBMS 186 and/or the host module 188. The OS 184 may be any operating system known in the art or which may be developed in the future including, but not limited to, Microsoft Windows®, Apple OSX™, Linux, Unix, Apple iOS™, Google Android™, or a mainframe operating system. The DBMS 186 may be a suitable software module that facilitates access and management of one or more databases that are utilized to store information that is utilized by the claims processor computer 108 in various embodiments of the disclosure. The host module 188 may initiate, receive, process, and/or respond to requests, such as healthcare transactions, from the host module 188 of the service provider computer 104. The claims processor computer 108 may include additional program modules for performing other pre-processing or post-processing methods described herein. Those of ordinary skill in the art will appreciate that the claims processor computer 108 may include alternate and/or additional components, hardware or software without departing from example embodiments of the disclosure.

The I/O interface(s) 178 may facilitate communication between the processors 174 and various I/O devices, such as a keyboard, mouse, printer, microphone, speaker, monitor, bar code reader/scanner, RFID reader, and the like. The one or more network interface(s) 180 may facilitate connection of the claims processor computer 108 to one or more suitable networks, for example, network 110 illustrated in FIG. 1. In this regard, the claims processor computer 108 may receive healthcare transactions and/or other communications from the service provider computer 104, and the claims processor computer 108 may communicate information associated with the processing and adjudication of the healthcare transactions to the service provider computer 104.

The network 110 may include any telecommunications and/or data network, whether public, private, or a combination thereof, including a local area network, a wide area network, an intranet, the Internet, intermediate handheld data transfer devices, and/or any combination thereof and may be wired and/or wireless, or any combination thereof. The network 110 may also allow for real time, offline, and/or batch transactions to be transmitted between or among the sponsor computer 102, the service provider computer 104 (including the eligibility services module 148), the pharmacy computer 106, the claims processor computer 108, and the database 128. Various methodologies as described herein, may be practiced in the context of distributed computing environments. Although the service provider computer 104 is shown for simplicity as being in communication with the sponsor computer 102, the pharmacy computer 106, the claims processor computer 108, or the database 128 via one intervening network 110, it is to be understood that any other network configurations are possible. For example, intervening network 110 may include a plurality of networks, each with devices such as gateways and routers for providing connectivity between or among the components of the system 100. Instead of or in addition to the network 110, dedicated communication links may be used to connect various devices in accordance with an example embodiment. For example, the service provider computer 104 may form the basis of network 110 that interconnects the sponsor computer 102, the service provider computer 104 (including the eligibility services module 148), the pharmacy computer 106, the claims processor computer 108, and the database 128.

Those of ordinary skill in the art will appreciate that the system 100 shown in and described with respect to FIG. 1 is provided by way of example only. Numerous other operating environments, system architectures, and device and network configurations are possible. Other system embodiments can include fewer or greater numbers of components and may incorporate some or all of the functionality described with respect to the system components shown in FIG. 1. For example, in an exemplary embodiment, the service provider computer 104 (or other computer) may be implemented as a specialized processing machine that includes hardware and/or software for performing the methods described herein. Accordingly, embodiments of the disclosure should not be construed as being limited to any particular operating environment, system architecture, or device or network configuration.

Operational Overview

Certain portions of the exemplary methods below will be described with reference to determining and communicating intervention services associated with medication therapy management program that may be available for a patient as part of the processing of a healthcare transaction. While the methods described below are described with reference to a prescription claim or billing request, each form of a healthcare transaction, such as a predetermination of benefits transaction, healthcare claim transaction, prescription claim or billing request, healthcare order transaction, or e-prescription transaction (i.e., electronic prescription order transaction, e-script, or e-prescription), should be individually read as being used in the methods described below. In addition, while certain methods below are described with reference to the intervention service being an MTM service, this is also for example only and all other intervention services should be individually read as being used in the methods below.

Figure 2:
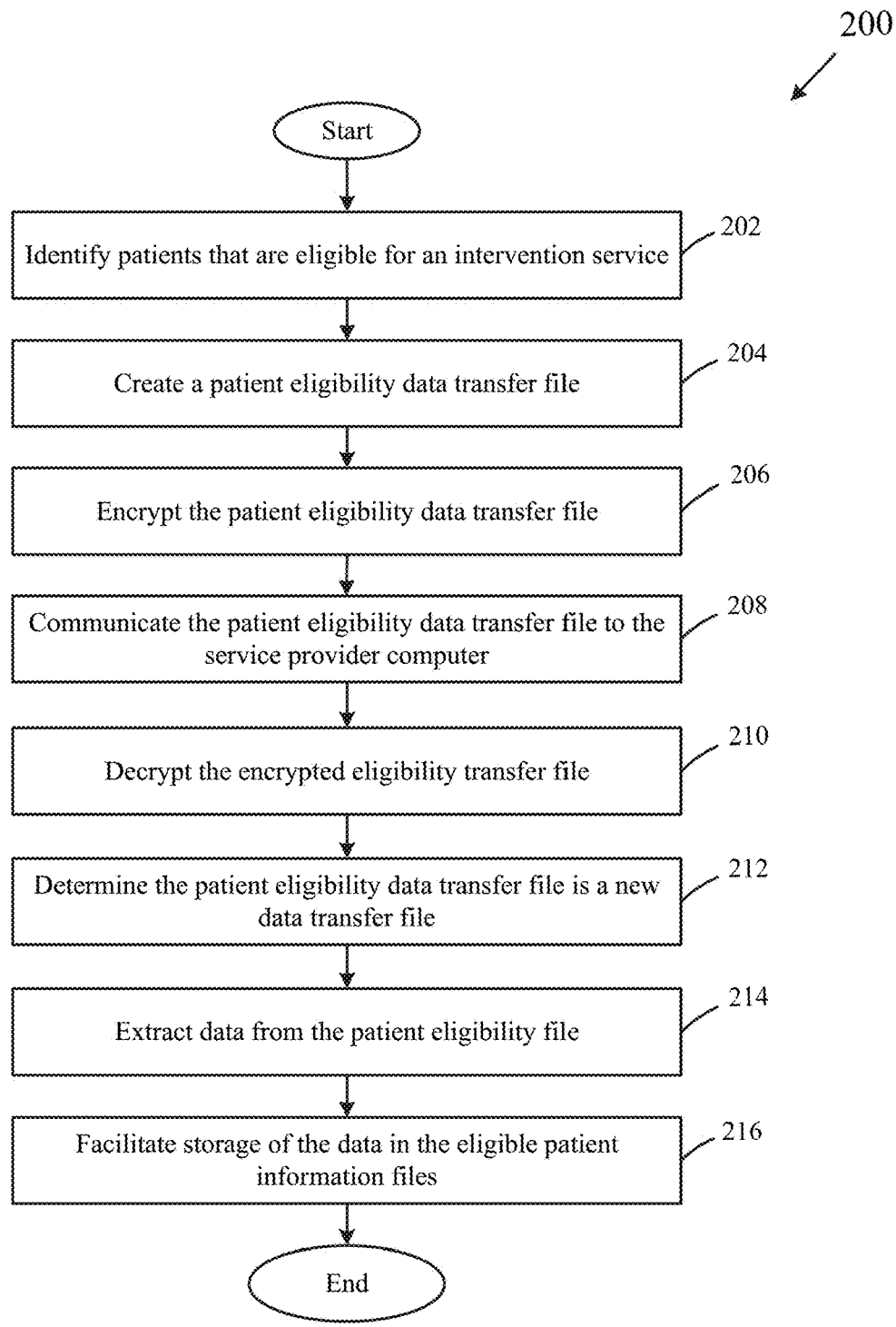
FIG. 2 illustrates a flow chart of an example method for accessing and/or communicating intervention services available for an eligible patient associated with a medication and/or product as part of the processing of a healthcare transaction, according to an example embodiment.

FIG. 2 is a flow chart illustrating an example method 200 for accessing and/or communicating intervention services available for an eligible patient associated with a medication and/or product as part of the processing of a healthcare transaction, according to an example embodiment of the disclosure. Referring now to FIGS. 1 and 2, the exemplary method 200 begins at the START step and continues to step 202, where a sponsor computer, such as sponsor computer 102, may identify one or more patients that may be eligible to receive one or more intervention services, such as a medication therapy management program. In one example implementation, a sponsor computer 102 may be associated with a healthcare entity (e.g., a healthcare services corporation) that has contracted with a pharmacy and/or a pharmacy corporation to provide a variety of intervention services including, but not limited to, MTM program services. An MTM service (also referred to herein as an intervention service) available to a patient may include a broad range of services. For example, without limitation, an intervention service may involve a patient assessment, a comprehensive medication review, formulating a medication treatment plan for a patient, enhancing medication adherence through patient education, monitoring efficacy and safety of medication therapy, and the like.

In one example implementation, a patient may be identified as an eligible patient based upon a medication and/or product association with an intervention service type. In one example implementation, the sponsor computer 102 may have access to a pharmacy's computer, such as pharmacy computer 106, and records associated with healthcare transactions (e.g., a predetermination of benefits transaction, healthcare claim transaction, prescription claim or billing request, healthcare order transaction, or e-prescription transaction (i.e., electronic prescription order transaction, e-script, or e-prescription). The sponsor computer 102 may identify from one or more accessed patient records, a patient that may be eligible to receive one or more intervention services. In one example implementation, the identification may be based upon a medication and/or product type (i.e., a medication/product identifier, a medication/product name, or the like) identified in an accessed patient record. Alternatively, the identification may be based upon a patient demographic such as, without limitation, a patient age and/or a patient gender.

At step 204, the sponsor computer 102 may create a patient eligibility transfer file for data associated with the identified patient. For example, based upon a predetermined file format, the sponsor computer 102 may create the patient eligibility transfer file. In one example implementation, the format for the patient eligibility transfer file may include one or more of the following information:

Header:
Segment ID: "HDR"
Post Date: 9(8)
File type: "Initial load"
Transaction:
Unique Patient ID
BIN Number:
Processor Control Number:
Group ID
Cardholder ID
Person Code
Patient Last Name
Patient First Name
Date of Birth
Social Security #(SSNID)
Patient Gender Code
Patient Street Address 1
Patient Street Address 2
Patient City Address
Patient State/Province Address Patient ZIP/Postal Zone
Primary Phone Number
Primary Phone Number Type
Alternate Patient Street 1
Alternate Patient Street 2
Alternate Patient City
Alternate Patient State
Alternate Patient ZIP
Alternate Patient Phone #
Alternate Patient Phone # Type
Eligibility Group:
Eligibility Type:
Eligibility Initiation:
Eligibility Termination:
Trailer:
Segment Identifier: "TRL"
Count: "NNNNNNN"

At step 206, the sponsor computer 102 may encrypt the created patient eligibility transfer file. In one example implementation, the encryption utilized by the sponsor computer 102 may be an encryption method predetermined by the sponsor computer 102, the service provider computer 104, and/or the pharmacy computer 106. For example, the encryption method may include, without limitation, hashing, private-key cryptography, public-key cryptography, or the like.

At step 208, the sponsor computer 102 may communicate an encrypted patient eligibility transfer file to the eligibility services module 148 or another portion of the service provider computer 104. At step 210, the eligibility services module 148 may decrypt the encrypted patient eligibility transfer file. In one example implementation, the eligibility services module 148 may receive, in, for example, a separate communication, means for decrypting the encrypted patient eligibility transfer file. For example, in a prior, subsequent, or concurrent communication, the eligibility services module 148 may receive a key necessary to decrypt the encrypted patient eligibility transfer file.

At step 212, the eligibility services module 148 may determine that the decrypted patient eligibility file is a file that contains new patient data. In one example implementation, the eligibility services module 148 may determine that the decrypted patient eligibility transfer file contains new data by parsing the header of the file. For example, the eligibility services module 148 may parse the header of the file and determine that the file type is an "initial load", meaning, the decrypted patient eligibility transfer file contains new patient data. In another non-limiting example, the patient eligibility data transfer file may be named in such a way as to indicate it is an initial setup file (e.g., File Name: "Initial Setup Patient Eligibility Data Transfer File").

At step 214, the eligibility services module 148 may extract the data from the patient eligibility transfer file. At step 216, the eligibility services module 148 may facilitate storage of the patient data included in the patient eligibility transfer file. In one example implementation, the extracted data may be stored in a file included in the one or more patient eligibility information files 150. The process may end following step 216.

Figure 3:
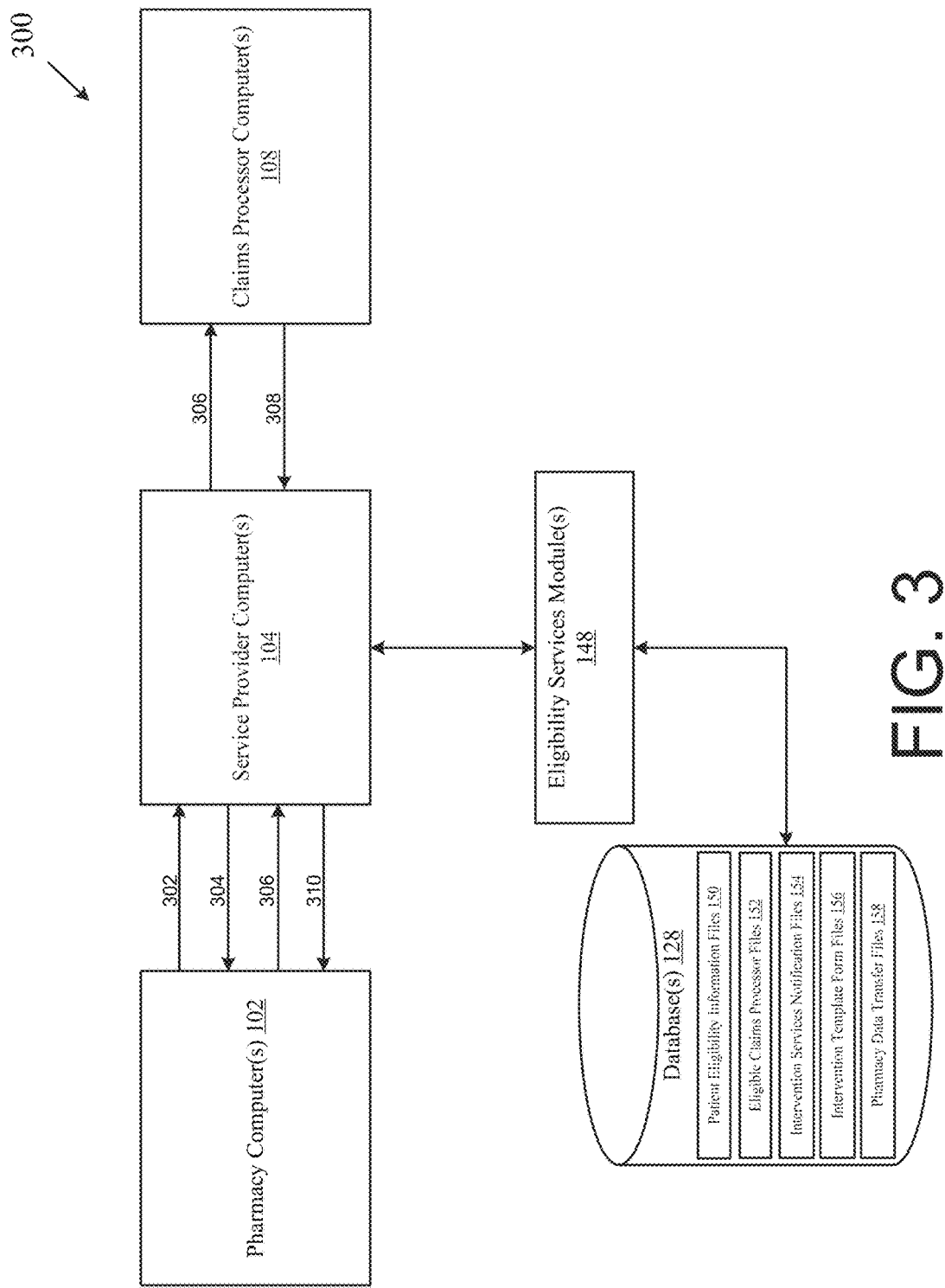
FIG. 3 illustrates an example block diagram for accessing, determining, and/or communicating notifications associated with available intervention services for an eligible patient as part of the processing of a healthcare transaction, according to an example embodiment.
Figure 4A:
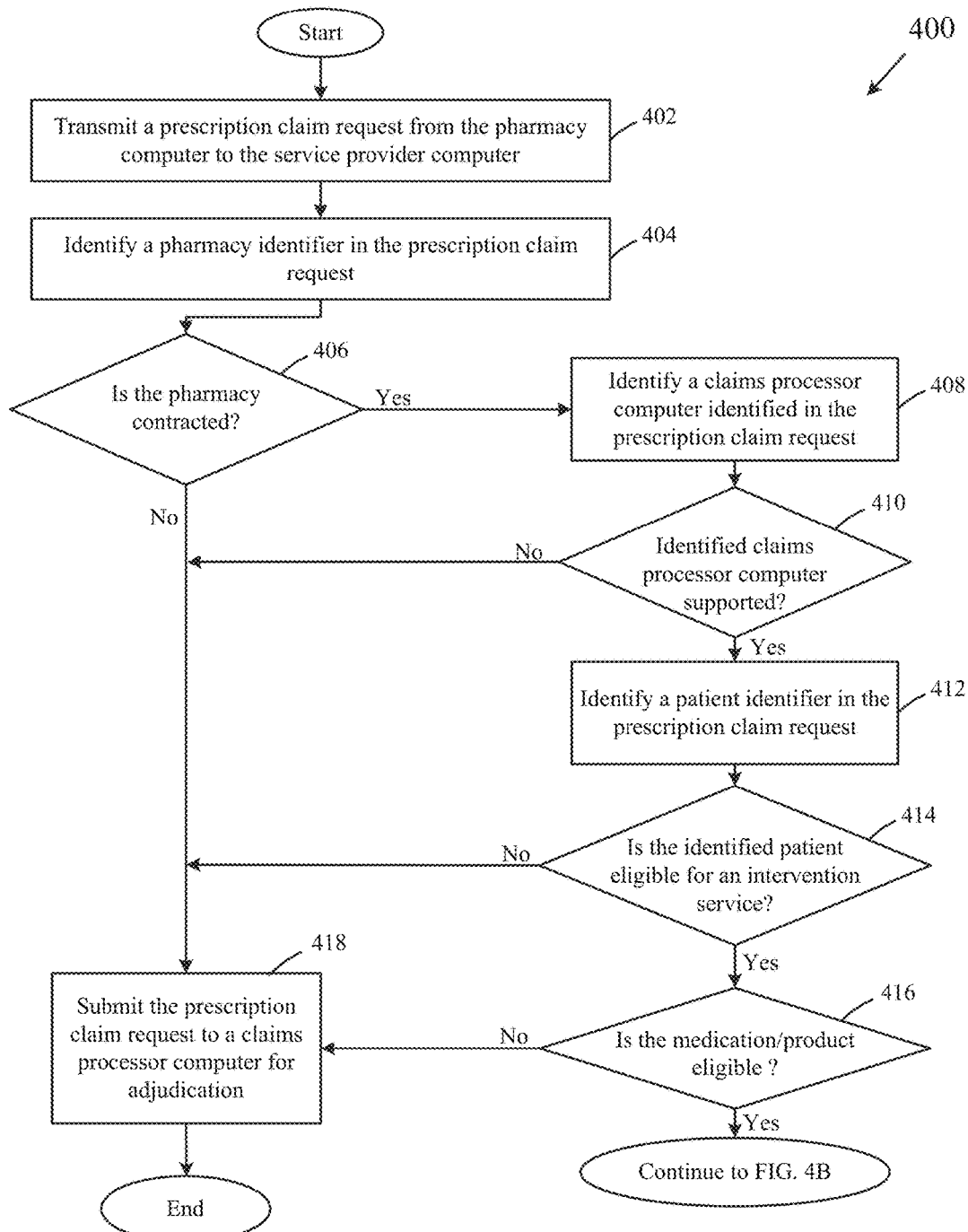
FIGS. 4A-E illustrate a flow chart of an example method for accessing, determining, and/or communicating notifications associated with available intervention services for an eligible patient as part of the processing of a healthcare transaction, according to one exemplary embodiment.
Figure 4B:
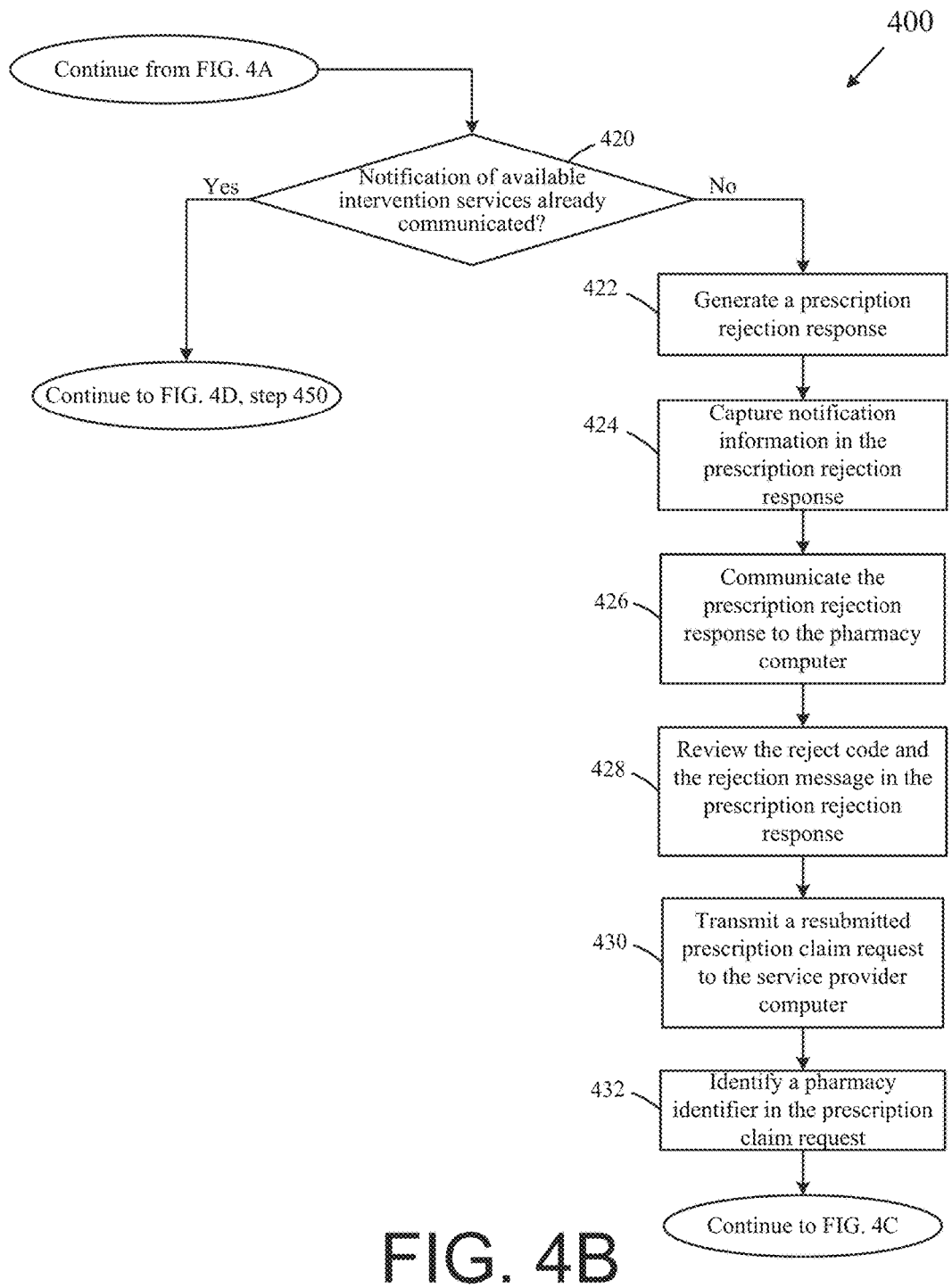
Figure 4C:
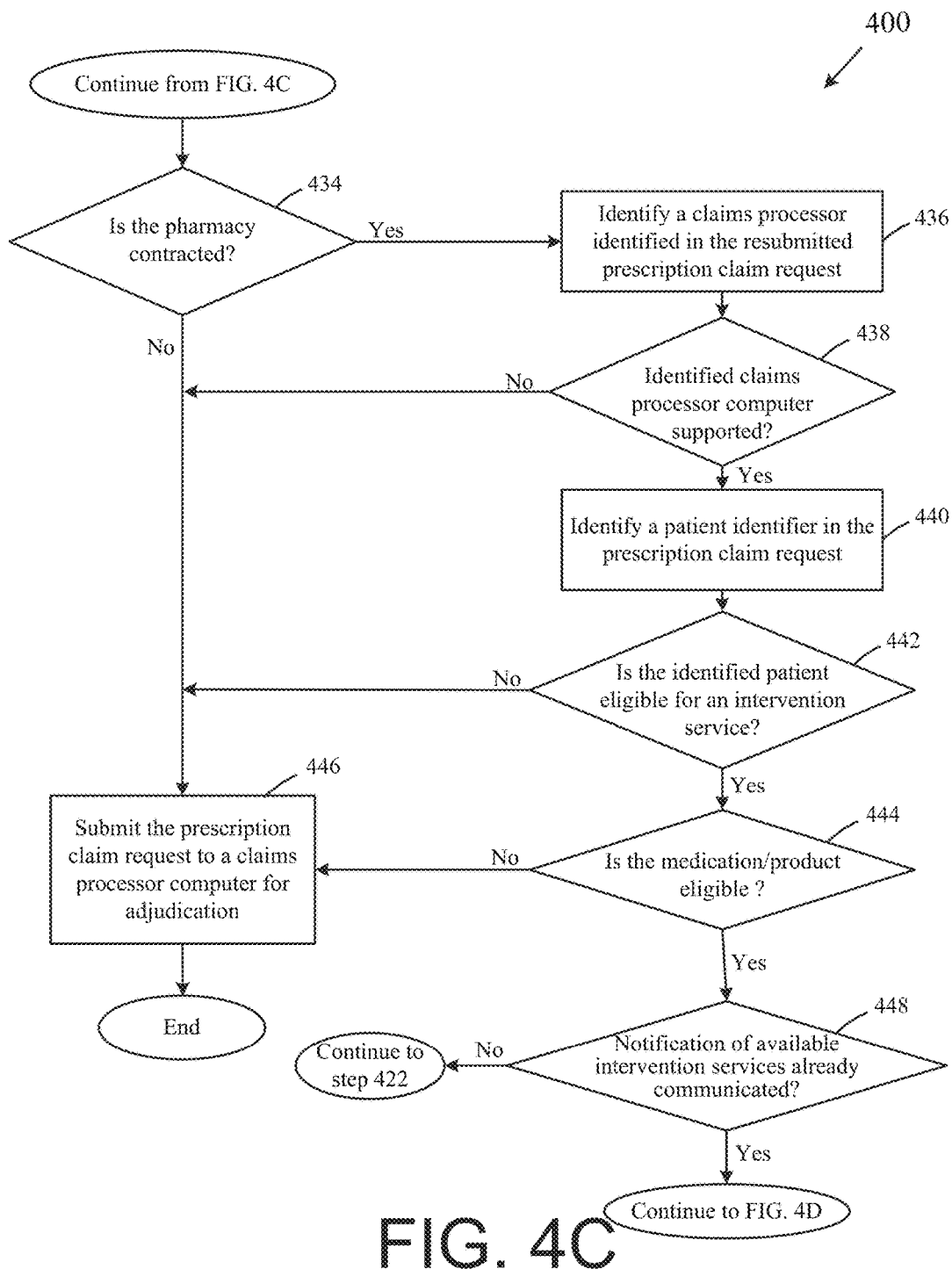
Figure 4D:
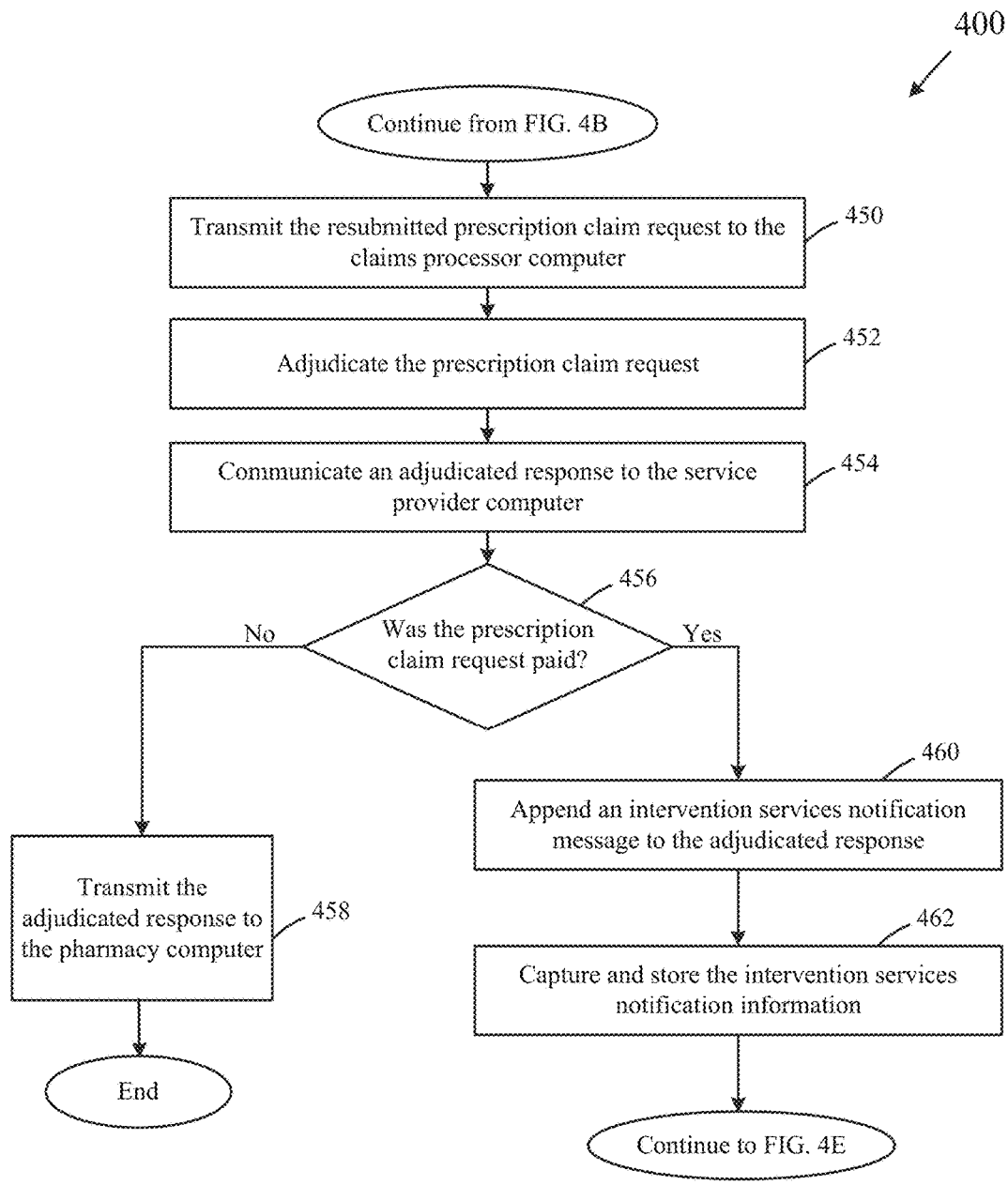
Figure 4E:
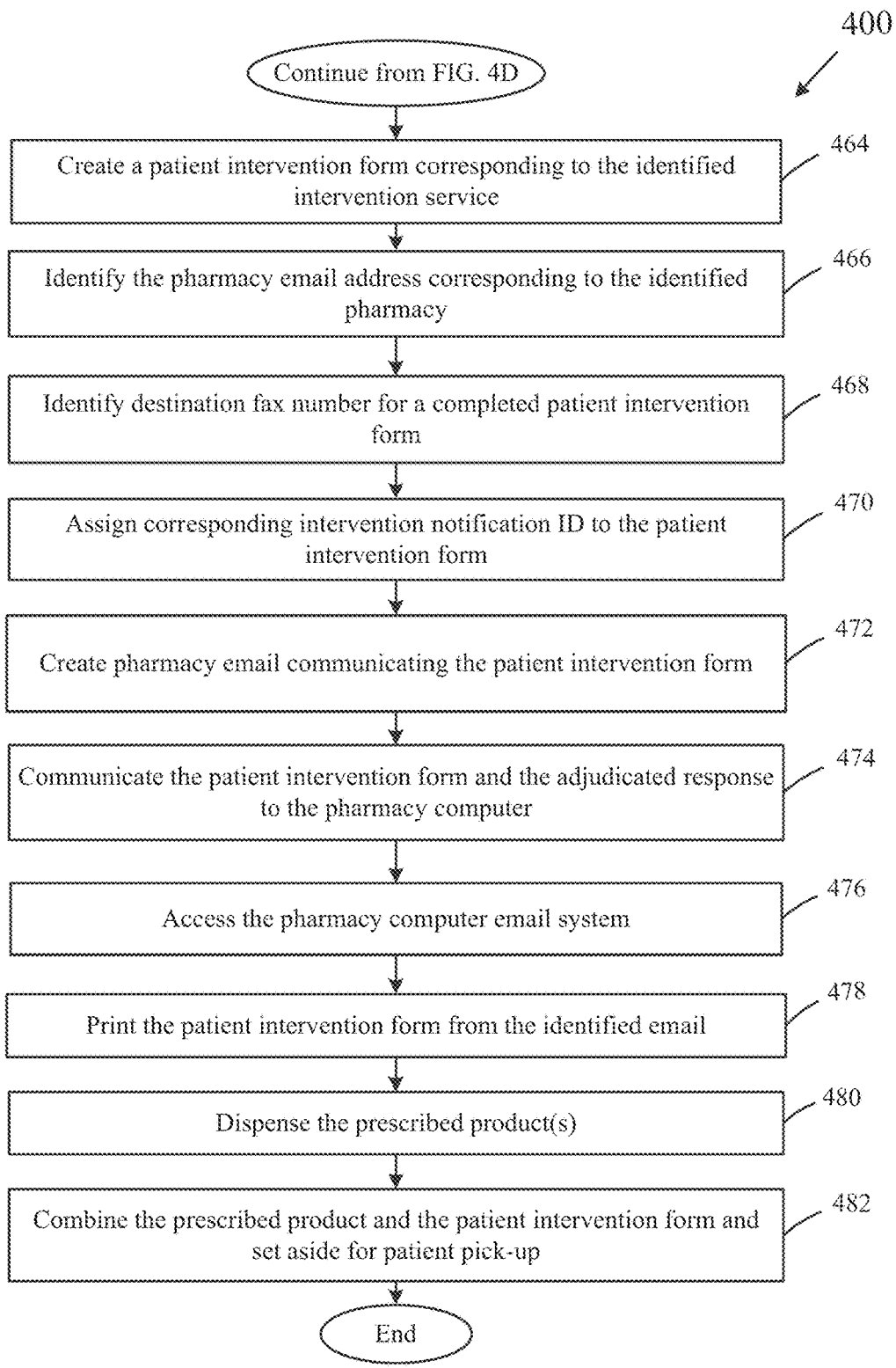

FIG. 3 illustrates an example block diagram for accessing, determining, and/or communicating notifications associated with available intervention services for an eligible patient as part of the processing of a healthcare transaction submitted by the pharmacy, according to an example embodiment of the disclosure. FIGS. 4A-E illustrate an example method 400 for accessing, determining, and/or communicating notifications associated with available intervention services for an eligible patient as part of the processing of a healthcare transaction submitted by the pharmacy via the pharmacy computer 106, according to an example embodiment of the disclosure. The block diagram 300 of FIG. 3 will be discussed in conjunction with the method 400 of FIG. 4A-E.

Referring now to FIGS. 1, 3, and 4A-E the exemplary method 400 begins at the START step and continues to step 402, where the pharmacy may transmit a prescription claim request 302 to the service provider computer 104. In one example implementation, the prescription claim request 302 may include a pharmacy financial transaction (i.e., a prescription billing request). The prescription claim request 302 may be in accordance with a version of the NCPDP Telecommunication Standard, although other standards may be utilized as well. As an example, the prescription claim request 302 may include one or more the following information:

Payor ID/Routing Information
    Transaction Payor Identifier(s) that designates a destination of the healthcare transaction 210 (e.g., BIN Number, BIN Number and PCN, or BIN Number and Group ID)
Patient Information
    Name (e.g. Patient Last Name, Patient First Name, etc.)
    Date of Birth of Patient
    Age of Patient
    Patient Gender Code
    Patient Address (e.g. Street Address, City, State/Province, Zip/Postal Code, etc.)
    Patient Contact Information (e.g. patient telephone number, email address, etc.)
    Patient ID or other identifier (e.g., Health Insurance Claim Number (HICN), social security number, etc.)
Insurance/Coverage Information
    Cardholder Name (e.g. Cardholder First Name, Cardholder Last Name)
    Cardholder ID and/or other identifier (e.g. person code)
    Group ID and/or Group Information
    State payor information
Provider Information
    Prescriber Information
    Primary Care Provider ID or other identifier (e.g., National Provider Identifier (NPI) code)
    Primary Care Provider Name (e.g. Last Name, First Name)
    Prescriber ID or other identifier (e.g. NPI code, Drug Enforcement Administration (DEA) number)
    Prescriber Name (e.g. Last Name, First Name)
    Prescriber Contact Information (e.g. Telephone Number)
    Pharmacy or other Healthcare Provider Information (e.g. store name, chain identifier, etc.)
    Pharmacy or other Healthcare Provider ID (e.g. NPI code)
Claim Information
    Drug, service, or product information (e.g. via NDC code or RxNorm code)
    Prescription/Service Reference Number
    Date Prescription Written
    Quantity Dispensed
    Days' Supply
    Diagnosis/Condition
    Pricing information for the drug/service/product (e.g. network price, Usual & Customary price)
    Number of Refills Authorized
    One or more Drug Utilization (DUR) Codes
    Dispense as Written (DAW)/Product Selection Code The prescription claim request 302 may be communicated to the service provider computer 104 via one or more suitable networks 110 (e.g., a wide area network, the Internet, a cellular network, etc.).

At step 404, the service provider computer 104 may identify a pharmacy identifier in the prescription claim request 302. In one example, the service provider computer 104 may parse the received prescription claim request 302 to identify a pharmacy identifier (i.e., a pharmacy name, NPI number, chain identifier, etc.) in one or more fields of the prescription claim request 302.

At step 406, the service provider computer 104 may process the prescription claim request 302. In one example, the processing of the prescription claim request 302 may include, without limitation, determining whether the pharmacy identified by the pharmacy identifier in the prescription claim request 302 is a contracted pharmacy. In one example implementation, a contracted pharmacy may be a pharmacy or group of pharmacies (e.g., pharmacy chain) that has contracted with the service provider associated with the service provider computer 104 to receive intervention services for the medications and/or products identified/requested in healthcare transactions, and thereby enable or activate the eligibility services module 148 for use in processing healthcare transactions, like the prescription claim request 302, that are routed or otherwise communicated to the service provider computer 104. For example, the service provider computer 104 may compare the identified pharmacy identifier (i.e., a pharmacy name, NPI code, pharmacy chain identifier, etc.) to a list of acceptable pharmacy identifiers for those pharmacies that have contracted to enable or activate the eligibility services module 148. If a match exists, the pharmacy identified by the pharmacy identifier in the prescription claim request 302 (e.g., the pharmacy associated with the pharmacy computer 106) is determined to be contracted, the eligibility services module 148 is determined to be activated for the current prescription claim request 302 and the YES branch is followed and processing may proceed to step 408. If a match is not identified, the pharmacy identified by the pharmacy identifier in the prescription claim request 302 (e.g., the pharmacy associated with the pharmacy computer 106) is not contracted, the eligibility services module 148 is determined to not be available for the prescription claim request 302, and the NO branch is followed and processing may proceed to step 418.

At step 408, processing of the prescription claim request 302 may further include an identification of a corresponding claims processor computer 108. In one example implementation, the service provider computer 104 may parse the prescription claim request 302 to identify at least a benefits provider identifier (e.g., BIN Number, BIN Number and PCN, or BIN Number and Group ID). At step 410, the service provider computer 104 may determine whether the identified claims processor computer 108 is supported by the system described in FIG. 1. In one example, the service provider computer 104 may compare the identified benefits provider identifier to one or more tables within the eligible claims processor files 152. The service provider computer 104 may parse the one or more tables within the eligible claims processor files 152 to identify whether the benefit provider identifier matches a claims processor listed in the eligible claims processor files 152. If the benefit identifier does exist in the eligible claims processor files 152, then a match has occurred and the YES branch is followed and processing may proceed to step 412. If the benefit provider identifier does not exist in the eligible claims processor files 152, then a match does not exist and the NO branch is followed and processing may proceed to step 418.

At step 412, processing of the prescription claim request 302 may further include an identification of one or more patient identifiers in the prescription claim request 302. In one example, the service provider computer 104 may parse the received prescription claim request 302 to identify one or more patient identifiers (i.e., a patient social security number, a subset of the patient social security number, health insurance claim number (HICN), cardholder ID, a patient first name, patient last name, patient date of birth, patient gender, patient address, patient zip/postal code, etc.).

At step 414, the service provider computer 104 may process the prescription claim request 302. In one example, the processing of the prescription claim request 302 may include, without limitation, determining whether the identified patient in the prescription claim request 302 is eligible for an intervention service. In one example implementation, the service provider computer 104 may employ the eligibility services module 148 to access the patient eligibility information files 150. The patient eligibility information files 150 may include information provided by the sponsor computer 102. For example, the patient eligibility information files 150 may include at least a patient ID, patient demographics (i.e., patient gender, patient age, patient date of birth, patient street address, patient zip/postal code etc.), an eligibility group, and/or an eligibility type. The eligibility services module 148 may compare the identified one or more patient identifiers from the prescription claim request 302 to the patient information in the patient eligibility information files 150. For example, the eligibility services module 148 may parse the patient eligibility information files 150 to determine if the identified one or more patient identifiers matches a patient identifier in the files 150. If a match exists, the patient is eligible for an intervention service and the YES branch is followed and processing may proceed to step 416. If a match is not identified, the patient is ineligible for an intervention service and the NO branch is followed and processing may proceed to step 418.

At step 416, processing of the prescription claim request 302 may further include a determination of whether the prescription claim request includes a request for an eligible medication/product. In one example embodiment, this determination can be made by the eligibility services module 148 or another portion of the service provider computer 104. In one example, an eligible product may include, without limitation, a product for which the eligibility services module 148 may determine to correspond with the eligibility group, the eligibility type, and/or the patient demographic information included in the patient eligibility information files 150. In one example, the service provider computer 104 may parse the prescription claim request 302 to identify one or more product/medication identifiers (e.g., NDC code, RxNorm code, medication name, etc.). Once a product/medication is identified, the service provider computer 104 may compare the identified product/medication to the information included in the associated patient eligibility information file (i.e., the eligibility group, the eligibility type, and/or the patient demographic information) to determine if a match exists. If a match does not exist, the identified product/medication is a non-eligible product/medication, and the NO branch is followed and processing may proceed to step 418. If a match exists, the identified product/medication is an eligible product/medication, and the YES branch is followed to step 420.

At step 418, the service provider computer 104 may continue processing the claim request by passing the request 302 to the claims processor computer 108 for adjudication. The claims processor computer 108 will adjudicate the request 302 and return and adjudicated response to the service provider computer 104. The service provider computer 104 can then transmit the adjudicated response to the pharmacy computer 106 without further intervention services evaluation. The method may end after step 418.

At step 420, processing of the prescription claim request may further include a determination of whether notification of the intervention service(s) available for the eligible patient have previously been communicated to the pharmacy. The determination may be based at least in part on whether the patient has previously received notification of the available intervention service(s). Alternatively and/or additionally, the determination may be based at least in part upon whether an override code has been submitted along with and/or is contained within the prescription claim request 302, and/or the prescription claim request 302 coincides with an interval between notification periods for the available service. In one example implementation, the service provider computer 104 may employ the eligibility services module 148 to access the intervention notification files 154. The eligibility services module 148 may compare the identified patient identifier to the patient information in the intervention notification files. For example, the eligibility services module 148 may parse the intervention notification files 154 to determine if the identified patient identifier matches a patient identifier in the intervention notification files 154. If a match is identified, the eligibility services module 148 may further determine whether the identified patient identifier found in the intervention notification files 154 includes a file for the corresponding available service(s). The determination may, for example, be based upon a medication and/or product identifier included in the identified file for the identified patient. Alternatively and/or additionally, the determination may be based upon a corresponding service(s) code or type included in the identified file associated with the available intervention service. If notification of the available service has previously been communicated to the pharmacy, then the YES branch is followed and processing may proceed to step 450. If a match does not exist and notification of the available service has not previously been communicated to the pharmacy, then the NO branch is followed and processing may proceed to step 422.

At step 422, the service provider computer may generate a prescription rejection response 304. In one example implementation, the service provider computer 104 may employ the eligibility services module 148 to insert or otherwise append an available intervention services notification to the prescription rejection response 304. The available intervention services notification and rejection response 304 may include at least a reject code indicating the reason why the prescription claim request 302 was rejected and/or a rejection message communicating to the pharmacist associated with the pharmacy computer 106 that intervention service(s) are available for the patient. For example, the prescription rejection response 304 may include:

Reject Code: "XX"
Message: "Intervention opportunity—resubmit claim, access pharmacy email if paid response follows, print patient intervention form, associate with prescription."

At step 424, the service provider computer 104 may capture that a notification for available intervention service(s) was communicated to the pharmacy computer 106. In one example implementation, the information associated with the notification may be captured and stored in the identified file in the intervention notification files 154. Alternatively and/or additionally, the information associated with the notification may be captured and stored in a patient eligibility information file 150 corresponding to the identified patient.

At step 426, the prescription rejection response 304 may be transmitted to the pharmacy computer 106 from the service provider computer 104 via, for example, the network 110. At step 428, the pharmacy computer can receive the prescription rejection response 304 and the pharmacist or other employee of the pharmacy associated with the pharmacy computer 106 may review the prescription rejection response 304. During the review of the prescription rejection response 304, the pharmacist, for example, may identify the reject code and the reject message included in the prescription rejection response 304. After reviewing the rejection message included in the prescription rejection response 304, at step 430, the pharmacy computer 106 may transmit a resubmitted prescription claim request 306 to the service provider computer 104. In one example implementation, the resubmitted prescription claim request 306 is the same as the prescription claim request 302 and may include the information described herein with respect to prescription claim request 302. The resubmitted prescription claim request 306 may be communicated to the service provider computer 104 via one or more suitable networks 110 (e.g., a wide area network, the Internet, a cellular network, etc.).

At step 432, the service provider computer 104 may identify a pharmacy identifier in the resubmitted prescription claim request 306. In one example, the service provider computer 104 may parse the resubmitted prescription claim request 306 to identify a pharmacy identifier (i.e., a pharmacy name, NPI number, chain identifier, etc.) in one or more fields of the resubmitted prescription claim request 306.

At step 434, the service provider computer 104 may process the resubmitted prescription claim request 306. In one example, the processing of the resubmitted prescription claim request 306 may include, without limitation, determining whether the pharmacy identified in the resubmitted prescription claim request 306 is a contracted pharmacy. In one example implementation, the determination may be similar to that described at step 406. If a match exists, the pharmacy identified by the pharmacy identifier in the request 306 and identifying the pharmacy computer 106 is determined to be contracted, the eligibility services module 148 is determined to be activated for the resubmitted prescription claim request 306 and the YES branch is followed and processing may proceed to step 436. If a match is not identified, the pharmacy associated with the pharmacy computer 106 is not contracted, the eligibility services module 148 is determined to not be available for the prescription claim request 302, and the NO branch is followed and processing may proceed to step 446.

At step 436, processing of the resubmitted prescription claim request 306 may further include an identification of a corresponding claims processor computer 108. In one example implementation, the service provider computer 104 may parse the resubmitted prescription claim request 306 to identify at least a benefits provider identifier (e.g., BIN Number, BIN Number and PCN, or BIN Number and Group ID). At step 438, the service provider computer 104 may determine whether the identified claims processor computer 108 is supported by the system described in FIG. 1. In one example implementation, the determination may be similar to that described at step 410. In one example, the service provider computer 104 may compare the identified benefits provider identifier to one or more tables within the eligible claims processor files 152. If the benefit identifier does exist in the eligible claims processor files 152, then the YES branch is followed and processing may proceed to step 440. If the benefit identifier does not exist in the eligible claims processor files 152, then the NO branch is followed and processing may proceed to step 446.

At step 440, processing of the resubmitted prescription claim request 306 may further include an identification of a patient. In one example, the service provider computer 104 may parse the received resubmitted prescription claim request 306 to identify a patient identifier (i.e., a patient social security number, a subset of the patient social security number, health insurance claim number (HICN), cardholder ID, a patient first name, patient last name, patient date of birth, patient gender, patient address, patient zip/postal code, etc.). At step 442, the service provider computer 104 may process the resubmitted prescription claim request 306. In one example, the processing of the resubmitted prescription claim request 306 may include, without limitation, determining whether the identified patient in the resubmitted prescription claim request 306 is eligible for an intervention service. In one example implementation, the determination may be similar to that described at step 414. If a match exists, the patient is eligible for an intervention service and the YES branch is followed and processing may proceed to step 444. If a match is not identified, the patient is ineligible for an intervention service and the NO branch is followed and processing may proceed to step 446.

At step 444, processing of the resubmitted prescription claim request 306 may further include a determination of whether the prescription claim request 306 includes a request for an eligible medication/product. In one example embodiment, this determination is similar to that described at step 416. If a match does not exist, the medication is a non-eligible product, and the NO branch is followed and processing may proceed to step 446. If a match exists, the identified product/medication is an eligible product/medication, and the YES branch is followed to step 448.

At step 446, the service provider computer 104 may continue processing the claim request by passing the resubmitted request 306 to the claims processor computer 108 for adjudication. The claims processor computer 108 will adjudicate the request 306 and return and adjudicated response to the service provider computer 104. The service provider computer 104 can then transmit the adjudicated response to the pharmacy computer 106 without further intervention services evaluation. The method may end after step 446.

At step 448, the processing of the resubmitted prescription claim request 306 may further include a determination of whether notification of the service(s) available for the eligible patient has been communicated to the pharmacy. The determination may be based at least in part on whether the patient has previously received notification of the available service. Alternatively and/or additionally, the determination may be based at least in part upon whether an override code has been submitted along with and/or is contained within the resubmitted prescription claim request 306, and/or the resubmitted prescription claim request 306 coincides with an interval between notification periods for the available service. In one example implementation, the service provider computer 104 may employ the eligibility services module 148 to access the intervention notification files 154. The eligibility services module 148 may compare the identified patient identifier to the patient information in the intervention notification files 154. For example, the eligibility services module 148 may parse the intervention notification files 154 to determine if the identified patient identifier matches a patient identifier in the files 154. If a match is identified, the eligibility services module 148 may further determine whether the identified patient identifier found in the intervention notification files 154 includes a file for the corresponding available service(s). The determination may, for example, be based upon a medication and/or product identifier included in the identified file for the identified patient. Alternatively and/or additionally, the determination may be based upon a service(s) code or type included in the identified file. If notification of the available service has previously been communicated to the pharmacy, then the YES branch is followed and processing may proceed to step 450. If a match does not exist and notification of the available service has not previously been communicated to the pharmacy, then the NO branch is followed and processing may proceed to step 422.

At step 450, the service provider computer 104 may transmit the resubmitted prescription claim request 306 to the claims processor computer 108 via, for example, the network 110 for adjudication. At step 452, the claims processor computer 108 may adjudicate the resubmitted prescription claim request 306. At step 454, the claims processor computer 108 may communicate an adjudicated response 308 to the service provider computer 104 via, for example, the network 110. The adjudicated response 308 may include, without limitation, a transaction status indicator indicating whether the resubmitted prescription claim request 306 was paid or rejected. In one example implementation, when the resubmitted prescription claim request 306 is paid, the adjudicated prescription claim response 308 may have a transaction status indicator "P". If, however, the resubmitted prescription claim request 306 is rejected, the adjudicated response 308 may have a transaction indicator "F".

In one example, when the adjudicated response 308 includes a transaction status indicator "P", the adjudicated response 308 may also include, without limitation, one or more fields comprising a patient pay amount field (the patient co-pay) populated with a value returned by the claims processor computer 108, an associated quantity dispensed field populated with a submitted quantity to be dispensed on the resubmitted prescription claim request 306, and/or a pharmacy name field populated with a short pharmacy name corresponding to the submitted pharmacy identifier on the resubmitted prescription claim request 306.

If, on the other hand, the adjudicated response 308 includes the transaction status indicator "F", the adjudicated response 308 may also include, without limitation, one or more fields comprising the patient pay amount field left blank, the associated dispensed quantity field left blank, a reject reason field populated with a reject code (e.g., pricing not available for an identified scenario, reject description, patient not covered, medication not in formulary, or the like), the pharmacy name field is left blank, a reason for service code field populated with a reject error code, and/or a reason for service description field populated with an abbreviated description of the corresponding reason for service code.

At step 456, the service provider computer 104 may determine whether the resubmitted prescription claim request 306 was approved for payment by the claims processor computer 108. In one example, the service provider computer 104 may parse the adjudicated response 308 to identify the transaction status indicator in the response 308. If the identified transaction status indicator is an "F", then the NO branch is followed and processing may proceed to step 458. If the identified transaction status indicator is a "P", then the YES branch is followed and processing may proceed to step 460.

If the adjudicated response 308 includes the transaction status indicator "F", at step 458 the service provider computer 104 may transmit the adjudicated response as part of a reject message 310 to the pharmacy computer 106. The reject message 310 may include one or more rejection reasons corresponding to the resubmitted prescription claim request 306 and/or one or more reject codes in the adjudicated response 308. The method may end after step 458.

In addition, the service provider computer 104 may perform any post-edits on the adjudicated response 308. For example, if the resubmitted prescription claim request 308 was paid or approved by the claims processor computer 108, at step 460, the service provider computer 104 may employ the eligibility services module 148 to append the adjudicated response 308 with a intervention services notification message. By way of example, the intervention services notification message may include:

Message: "Intervention opportunity—access pharmacy email, print patient intervention form, associate with prescription."

At step 462, the service provider computer 104 may capture and store information associated with the one or more fields included in the adjudicated response 308. In one example implementation, the captured information may include the intervention services notification message. The eligibility services module 148 and/or other components of the service provider computer 104 may facilitate storage of the intervention services notification message along with the identified patient information and the identified pharmacy information in the intervention services notification files 154. The captured information may be organized such that the intervention services notification information may be accessed by the eligibility services module 148 and/or any other components of the service provider computer 104 when requested by the sponsor computer 102, the service provider computer 104, and/or the pharmacy computer 106. For example, the captured information may be organized in the intervention services notification files 154 according to an intervention notification ID assigned by the eligibility services module 148 or another portion of the service provider computer. In one example implementation, the intervention notification ID may a numeric value (e.g., 1234), a letter designation (e.g., ABCD), or an alphanumeric value (e.g., 1234AB).

Figure 6:
FIG. 6 illustrates a representative patient service form, according to one exemplary embodiment.

At step 464, the service provider computer 104 may create a patient intervention form corresponding to the identified available intervention service. In one example implementation, the service provider computer 104 may employ the eligibility services module 148 to access one or more intervention form templates in the intervention template forms file 156. For example, a patient information form may be similar to template 602 illustrated in FIG. 6. As illustrated in template 602, the patient information form may include, without limitation, one or more fields including a patient first name, a patient last name, a patient date of birth, a prescription number, a pharmacy ID, and a prescriber's last name available in the resubmitted prescription claim request 306 and/or the adjudicated response 308.

The template 602 may also include information that may be communicated from the pharmacist to the patient. The information may be used to educate and/or re-educate the patient on the importance of medication management. For example, the identified medication may be a medication used to treat hypertension (i.e., Lisinopril). The template 602 may include information associated with hypertension that may be communicated to the patient. For example, the template may include facts and/or statistics associated with hypertension, symptoms associated with hypertension, and/or or why the patient may not be compliant with their medication.

The eligibility services module 148 or another portion of the service provider computer 104 may populate the accessed patient intervention form template 602 with information from the resubmitted prescription claim request 306, the adjudicated response 308, or a combination thereof. For example, the eligibility services module 148 may identify at least the patient first name, the patient last name, a patient date of birth, and a prescription/service reference number from the resubmitted prescription claim request 306 and/or the adjudicated response 308.

At step 466, the service provider computer 104 may identify an email address corresponding to the pharmacy identified in the resubmitted prescription claim request 306. In one example implementation, the service provider computer 104 may employ the eligibility services module 148 to access a pharmacy data transfer file 158. The pharmacy data transfer file may include, without limitation, previously supplied pharmacy data supporting transmission information. By way of example, the pharmacy data transfer file may include one or more of:

Header:
Segment ID: "HDR"
File Name: "PharmacyEmailAddress"
Sponsor ID: "VARCHAR2(10)"
Sponsor Name: "VARCHAR2(30)"
Date/Time: MMddccyyHHmmss
File Type: "Initial"
Transaction:
Segment Identifier: "DTL"
NCPDP Provider ID:
NPI:
Email address:
Fax number:
Store name:
Chain name:
Primary Phone number:
Secondary Phone number:
Trailer:
Segment Identifier: "TRL"
Count: "NNNNNNN"

In one example implementation, the eligibility services module 148 may compare the identified pharmacy identifier from the resubmitted prescription claim request 306 and/or the adjudicated response 308 to the pharmacy identifiers (i.e., NPI codes) of the one or more pharmacy data transfer files 158. Once a pharmacy data transfer file 158 has been identified as being a match to the pharmacy identifier, the eligibility services module 148 may access the file and extract the pharmacy email address.

At step 468, the service provider computer 104 may identify the destination facsimile ("fax") telephone number for the patient intervention form. For example, the destination fax number may be utilized by a pharmacist associated with the identified pharmacy to return a patient intervention form completed by the patient. At step 470, the service provider computer 104 may assign an intervention notification ID to the created patient intervention form. In one example implementation, the intervention notification ID assigned to the patient intervention form is the same as the intervention notification ID assigned to the information captured and stored at step 462.

At step 472, the service provider computer 104 may create an email message to communicate the patient intervention form to the identified pharmacy. While, in one example embodiment, the communication is described as an email communication, it is to be appreciated that the means for communication may include other forms such as, for example, mail, fax, text (e.g., SMS or MMS), etc. In one example implementation, the email may include a subject line identifying the corresponding prescription number from the resubmitted prescription claim request 306 or the adjudicated response 308. For example, the subject line of the email may read "Intervention for RX #NNNNNNN".

At step 474, the service provider computer 104 may communicate the email message, including the patient intervention form, to the identified pharmacy computer 106. At step 476, a pharmacist at a pharmacy associated with the pharmacy computer 106 may access the pharmacy email system and identify the email corresponding to the adjudicated response 308. For example, the pharmacist may identify the prescription number in the adjudicated response 308 and compare the prescription number to the prescription number(s) found in the subject line of one or more emails.

At step 478, the pharmacist at the pharmacy associated with the pharmacy computer 106 may print the patient intervention form included in (e.g., attached to) the identified email. At step 480, the pharmacist may dispense the medication and/or product. The dispensed medication and/or product may be combined with the printed patient intervention form and set aside for patient pick-up.

Figure 5A:
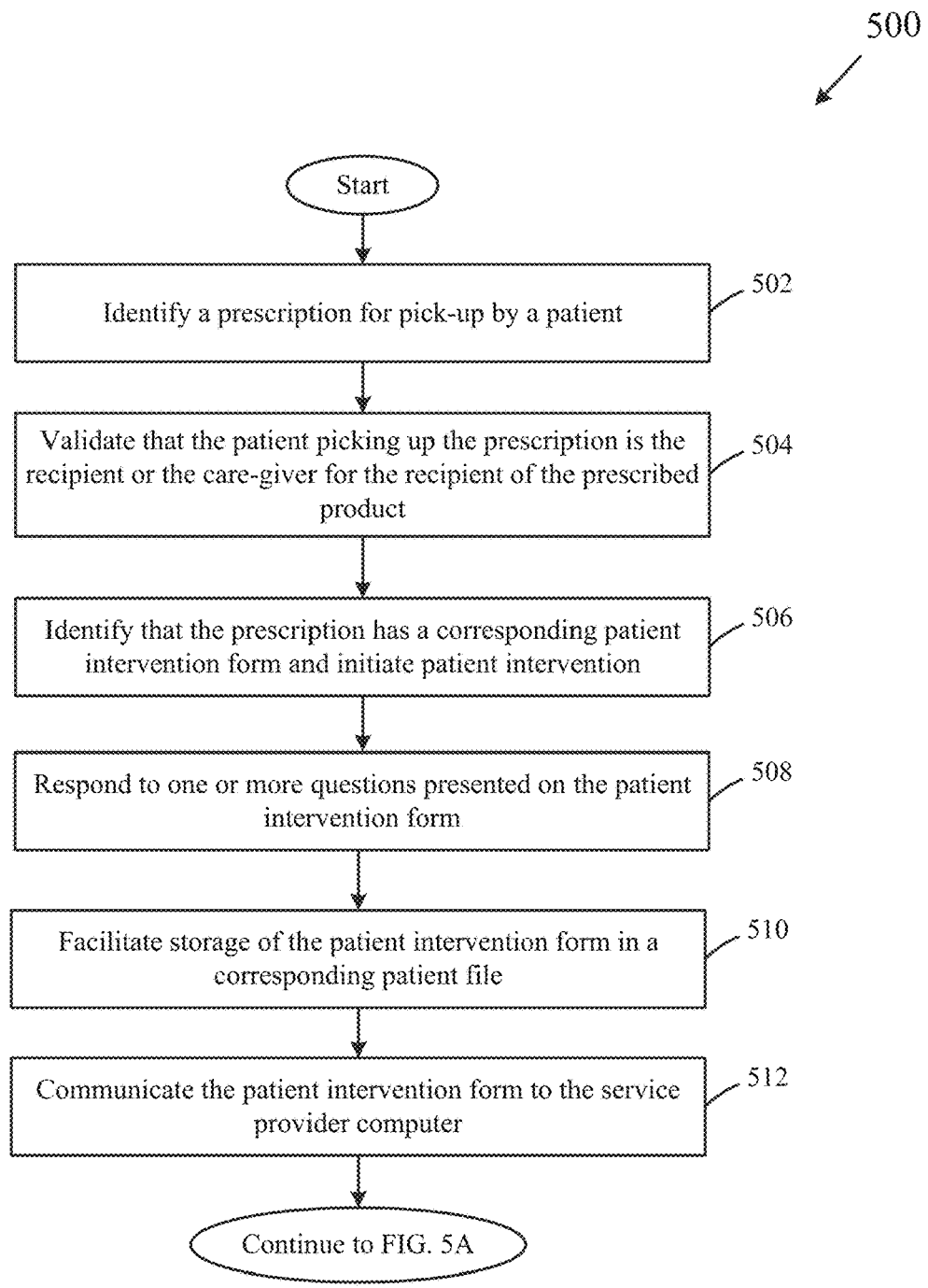
FIGS. 5A-B illustrate a flow chart of an example method for completing, processing and/or communicating patient intervention forms associated with a healthcare transaction, according to one exemplary embodiment.
Figure 5B:
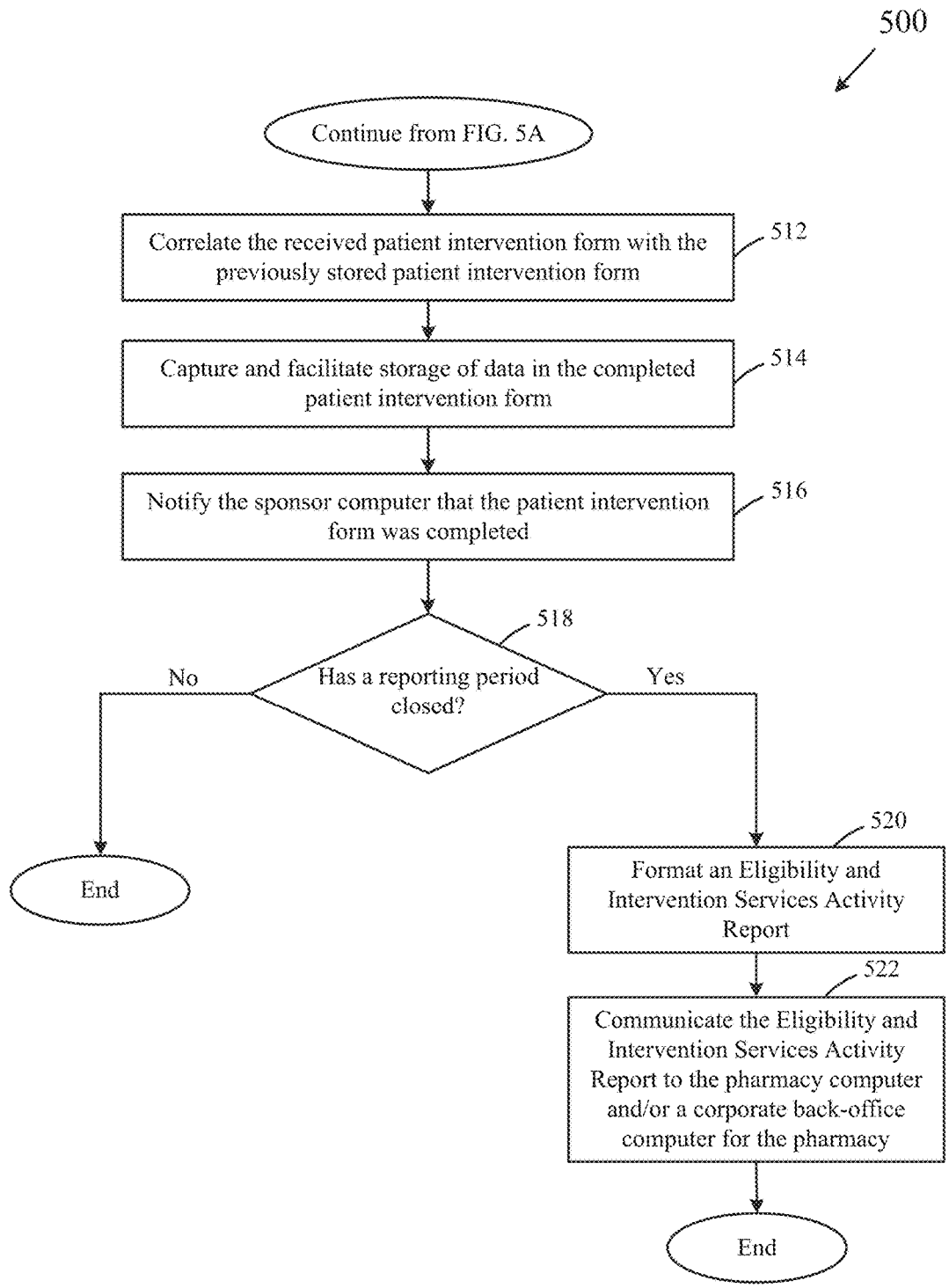

FIGS. 5A and 5B illustrate a flow chart of an example method 500 for completing, processing and/or communicating patient intervention forms associated with a healthcare transaction, according to an example embodiment of the disclosure.

Referring now to FIGS. 1, 3, 4A-E, and 5A-B the exemplary method 500 begins at the START step and continues to step 502, where a pharmacist at the pharmacy associated with a pharmacy computer 106 may identify a prescription for pick-up by a patient or patient caregiver. In one example implementation, the identification may be based upon a patient's first name, a patient's last name, a patient's birth date, a combination thereof, or the like. At step 504, the pharmacist may validate that the patient or patient caregiver picking up the identified prescription is the intended recipient or the caregiver for the intended recipient of the identified prescription. In one example implementation, the pharmacist may validate the identity of the individual using picture identification (i.e., a driver's license, a state identification, a military card, a passport, etc.). If the individual picking up the prescription is a caregiver for the patient, the caregiver may be asked to provide, in addition to picture identification, a form of authorization (i.e., a power of attorney, a notarized authorization from the patient and/or the prescriber, etc.), authorizing the caregiver to pick up the prescription.

At step 506, the pharmacist at the pharmacy associated with the pharmacy computer 106 may identify that the prescription being picked up has a corresponding patient intervention form. For example, as described at least in FIG. 4 at step 480, the pharmacist may have previously accessed and attached to the prescription, a patient intervention form. As such, during the pick-up of the prescription, the pharmacist may identify that the prescription includes a patient intervention form and initiate a patient intervention (e.g., MTM).

At step 508, the patient may respond to one or more questions presented on the patient intervention form. For example, as illustrated in patient intervention form 602 of FIG. 6, the patient intervention form may include one or more questions intended to elicit a response from a patient or patient caregiver. In addition, a patient intervention form may also include one or more informational points that may be presented/discussed by the pharmacist to the patient or patient caregiver at the time the prescription is picked up by the patient or the patient caregiver (e.g., at the point of sale). The pharmacist may also respond to any questions that the patient or the patient caregiver may have, and the patient or patient caregiver signs and dates a completed patient intervention form. In certain example embodiments, the pharmacist may also sign and date the completed patient intervention form.

At step 510, the pharmacy computer 106 may facilitate storage of the completed patient information form in a patient file. For example, the patient intervention form may be scanned or photographed by the pharmacy computer 106 or a device communicably coupled to the pharmacy computer and stored. At step 512, the pharmacist and/or the pharmacy computer 106 may transmit the completed patient intervention form to the service provider computer 104. In one example implementation, the pharmacist may communicate the completed patient intervention form to the service provider computer 104 via fax or eFax. For example, a destination fax number may be identified on the patient intervention form that was communicated to the pharmacy. The fax may be communicated to the service provider computer 104 at the time the patient intervention form is completed. Alternatively, the completed patient intervention form may be set aside at the pharmacy, and a batch of completed patient intervention forms may be communicated to the service provider computer 104. At the time of communication, the pharmacy computer 106 may also facilitate storage of the completed patient intervention form in data files 168 and/or the database 128.

At step 514, the service provider computer 104 may correlate the received completed intervention form with the previously stored patient intervention form. In one example implementation, the service provider computer 104 may employ the eligibility services module 148 or another portion of the service provider computer to identify the intervention notification ID on the completed patient intervention form. The eligibility services module 148 may compare the identified intervention notification ID on the completed form with one or more intervention notification ID's previously stored in the intervention notification files 154 to determine if a match exists. The eligibility services module 148 may identify an intervention notification file corresponding to the identified intervention notification ID based, at least in part on an identified match to the identified intervention notification ID. The eligibility services module 148 may capture and facilitate storage of data included in the completed patient intervention form in the identified intervention notification file 154.

At step 516, the service provider computer 104 may transmit a notification to the sponsor computer 102 that the patient intervention information was captured and stored. In one example implementation, the notification to the sponsor computer 102 may include the intervention notification ID, the patient name, and/or the date the form was completed. At step 518, the service provider computer 104 may determine if a period for reporting patient intervention information has closed. In one example implementation, the closing of the reporting period is configurable within the system and, in certain example embodiments, a reporting period may close on a last day of a week, the last day of a calendar month, a last day of a quarter, a last day of a calendar year, or any reasonable time period. If the service provider computer 104 determines that the reporting period has not closed, then the NO branch is followed, no further processing is needed, and the method 500 may end. If the service provider computer 104 determines that the reporting period has closed, then the YES branch is followed and processing may proceed to step 520.

At step 520, the service provider computer 104 may format a service report communicating intervention information. In one example implementation, the service provider computer 104 may format an "Eligibility & Intervention Services Activity Report" that may include one or more of:
  Header:
  Report Name: Eligibility & Intervention Services Activity
  Date Range: [Month], [Year]
  Intervention Notifications: NNN, NNN
  Completed Patient Intervention Forms: NNN, NNN
  Percentage Completed: XX.XX %
  Detail:
  Notification Date: NN/NN/NNNN
  Service Provider ID: [NPI]
  Prescription/Service Reference Number: "NNNNNNNN"
  Patient Intervention Form #: "XXXXXXXX"
  Submitted: "Y" or "N"

At step 522, the service provider computer 104 may transmit the service report to a back office corporate computer (not illustrated in FIG. 1) associated with the pharmacy computer 106. The method 500 may end after step 522.

Accordingly, example embodiments disclosed herein can provide the technical effects of creating a system and methods that provide a way to determine and communicate intervention service opportunities, such as those associated with medication therapy management, that may be available for a patient and to assist in the reporting and storage of documentation associated with completed intervention services as part of the processing of a healthcare transaction.

While certain example embodiments disclosed herein describe the eligibility services module 148 as a processor device separate from the service provider computer 104, in alternate embodiments the eligibility services module 148 or the functions that it completes may be incorporated into the service provider computer 104. In those alternate embodiments and with regard to the methods described above, the steps describing transmitting or receiving between the service provider computer 104 and the eligibility services module 148 may be internal transmissions within the service provider computer or may be omitted altogether. Further, while the exemplary embodiments described herein disclose certain steps occurring at the service provider computer 104 and/or the eligibility services module 148, in alternative embodiments those steps described with reference to FIGS. 1-6 may alternately be completed at the sponsor computer 102, the pharmacy computer 106, the claims processor computer 108, a combination of those devices, and/or a combination of those devices along with the service provider computer 104. In those alternate embodiments, certain transmission/receiving steps described above with reference to FIGS. 1-6 may be omitted while others may be added, as understood by one of ordinary skill in the art. The intent being that in alternate embodiments, any of the devices/computers discussed in FIG. 1 are capable of completing any or any part of the methods described with reference to FIGS. 2-5.

Various block and/or flow diagrams of systems and methods and/or computer program products according to example embodiments are described above. It will be understood that one or more blocks of the block diagrams and flow diagrams, and combinations of blocks in the block diagrams and flow diagrams, respectively, can be implemented by computer-executable program instructions. Likewise, some blocks of the block diagrams and flow diagrams may not necessarily need to be performed in the order presented, or may not necessarily need to be performed at all, according to some embodiments.

These computer-executable program instructions may be loaded onto a special purpose computer or other particular machine, a processor, or other programmable data processing apparatus to produce a particular machine, such that the instructions that execute on the computer, processor, or other programmable data processing apparatus create means for implementing one or more functions specified in the flowchart block or blocks. These computer program instructions may also be stored in a computer-readable memory that can direct a computer or other programmable data processing apparatus to function in a particular manner, such that the instructions stored in the computer-readable memory produce an article of manufacture including instruction means that implement one or more functions specified in the flow diagram block or blocks. As an example, embodiments of the disclosure may provide for a computer program product, that includes a computer usable medium (e.g., transitory or non-transitory) having a computer-readable program code or program instructions embodied therein, said computer-readable program code adapted to be executed to implement one or more functions specified in the flow diagram step or steps. The computer program instructions may also be loaded onto a computer or other programmable data processing apparatus to cause a series of operational elements or steps to be performed on the computer or other programmable apparatus to produce a computer-implemented process such that the instructions that execute on the computer or other programmable apparatus provide elements or steps for implementing the functions specified in the flow diagram step or steps.

Accordingly, blocks of the block diagrams and flow diagrams support combinations of means for performing the specified functions, combinations of elements or steps for performing the specified functions and program instruction means for performing the specified functions. It will also be understood that each block of the block diagrams and flow diagrams, and combinations of blocks in the block diagrams and flow diagrams, can be implemented by special-purpose, hardware-based computer systems that perform the specified functions, elements or steps, or combinations of special purpose hardware and computer instructions.

Many modifications and other embodiments of those set forth herein will be apparent having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. A computer-implemented method, comprising:
  receiving, by one or more service provider computers comprising a switch or a router and associated with a service provider, a first prescription claim transaction for a prescribed product prescribed to a patient and to be filled by a pharmacy, the first prescription claim transaction comprising a prescription number, a product identifier for the prescribed product, a patient identifier for the patient prescribed the prescribed product, a pharmacy identifier, and a claims processor identifier;

determining, by the one or more service provider computers and based at least on the patient identifier in the first prescription claim transaction, at least one intervention service is available for the patient;

determining, by the one or more service provider computers and after receipt of the first prescription claim transaction, if an available intervention service notification associated with the at least one available intervention service was previously transmitted to a pharmacy computer for the patient at a time prior to receiving the first prescription claim transaction, wherein determining if an available intervention service notification was previously transmitted comprises parsing intervention notification files stored in a database to determine if the patient identifier matches a patient identifier in the intervention notification files, and in response to the patient identifier matching a patient identifier in the intervention notification files, determine if the intervention notification files include a file having the matching patient identifier corresponding to the available intervention service;

generating, by the one or more service provider computers and based on a determination that the available intervention service notification has not been previously transmitted, a rejection response for the prescription claim transaction;

transmitting, by the one or more service provider computers to the pharmacy computer, the rejection response, the response comprising the available intervention service notification, wherein the one or more service provider computers comprises one or more memory devices configured to store data files that include a routing table to identify a destination of communications and a network interface to facilitate connection of the one or more service provider computers with one or more networks;

generating, by the one or more service provider computers, a patient intervention service form corresponding to the at least one available intervention service for the patient, wherein generation of the patient intervention service form comprises:
  retrieving, from a storage database, a patient intervention service template comprising standardized information to be applied to each of a plurality of intervention types; and
  populating, by the one or more service provider computers, the patient intervention service template based on an intervention type associated with the available intervention service and with patient information included in the first prescription claim transaction, the populated information comprising at least the prescription number, the patient name, and the pharmacy identifier, wherein the generated patient intervention service form comprises at least one element requiring patient input for completion;

transmitting, by the one or more service provider computers and separate from the rejection response, the patient intervention service form corresponding to the at least one available intervention service for the patient to the pharmacy computer to facilitate provision of an indication of availability of the patient intervention form to a pharmacist in response to receiving a request for the prescription from the patient or an associated patient caregiver in order to permit completion of the patient intervention service form by the pharmacist; and receiving, by the one or more service provider computers from the pharmacy computer, a completed patient intervention service form corresponding to the transmitted patient intervention service form, wherein the completed patient intervention service form comprises at least one element completed with patient input.

2. The computer-implemented method of claim 1, further comprising:
  determining, by the one or more service provider computers and after receipt of the first prescription claim transaction, that the available intervention service notification associated with the at least one available intervention service has previously been transmitted to the pharmacy computer at the time prior to receiving the first prescription claim transaction;
  transmitting, by the one or more service provider computers and in response to a positive determination that the at least one available intervention service has previously been transmitted to the pharmacy computer at the time prior to receiving the first prescription claim transaction, the first prescription claim transaction to a claims processor computer for adjudication; and
  receiving, by the one or more service provider computers from the claims processor computer, an approved adjudicated healthcare claim transaction response for the first prescription claim transaction.

3. The computer-implemented method of claim 2, further comprising:
  transmitting, by the one or more service provider computers to the pharmacy computer, the adjudicated prescription claim transaction response.

4. The computer-implemented method of claim 1, further comprising:
  receiving, by the one or more service provider computers, a plurality of intervention service forms comprising at least the completed patient service form;
  determining, by the one or more service provider computers, that an available intervention services reporting period has closed; and
  generating, by the one or more service provider computers, an available intervention services report comprising patient information collected from the plurality of intervention service forms.

5. The computer-implemented method of claim 1, wherein determining that at least one intervention service is available for the patient identified in the first prescription claim transaction comprises one or more of: (i) determining whether the product identifier identifies an eligible product, (ii) determining whether the pharmacy identifier identifies an eligible pharmacy, or (iii) determining whether a benefits provider identifier identifies an eligible claims processor.

6. The computer-implemented method of claim 1, further comprising accessing, by the one or more service provider computers, a patient intervention service file corresponding to the patient identifier in the first prescription claim transaction, wherein the patient intervention service file comprises one or more intervention service types available to the patient identified in the first prescription claim transaction.

7. The computer-implemented method of claim 1, wherein the completed patient intervention service form comprises at least a patient signature and a date associated with the patient signature.

8. The computer-implemented method of claim 1, wherein the at least one available intervention service for the patient is a medication therapy management service.

9. A system comprising a switch or a router, the system comprising:
- at least one memory operable to store computer-executable instructions and configured to store data files that include a routing table to identify a destination of communications;
- a network interface to facilitate connection with one or more networks; and
- at least one processor configured to access the at least one memory and execute the computer-executable instructions to:
  - receive, from a pharmacy computer for a pharmacy, a first prescription claim transaction for a prescribed product prescribed to a patient and to be filled by the pharmacy, the first prescription claim transaction comprising a prescription number, a product identifier for the prescribed product, a patient identifier for the patient prescribed the prescribed product, a pharmacy identifier, and a claims processor identifier;
  - determine, based at least on the patient identifier in the first prescription claim transaction, that at least one intervention service is available for the patient;
  - determine, after receipt of the first prescription claim transaction, if an available intervention service notification associated with the at least one available intervention service was previously transmitted to a pharmacy computer for the patient at a time prior to receiving the first prescription claim transaction wherein the computer executable instructions to determine if an available intervention service notification was previously transmitted comprises computer executable instructions to parse intervention notification files to determine if the patient identifier matches a patient identifier in the intervention notification files, and in response to the patient identifier matching a patient identifier in the intervention notification files, determine if the intervention notification files include a file having the matching patient identifier corresponding to the available intervention service;
  - generate, based on a determination that the available intervention service notification has not been previously transmitted, a rejection response for the prescription claim transaction;
  - transmit the rejection response to the pharmacy computer based on the stored routing table, the rejection response comprising the available intervention service notification;
  - generate a patient intervention service form corresponding to the at least one available intervention service for the patient, wherein generation of the patient intervention service form comprises:
    - computer executable instructions to retrieve, from a storage database, a template comprising standardized information to be applied to each of a plurality of intervention types; and
    - computer executable instructions to populate, by the one or more service provider computers, the patient intervention service template based on an intervention type associated with the available intervention service and with patient information included in the first prescription claim transaction, the populated information comprising at least the prescription number, the patient name, and the pharmacy identifier, wherein the generated patient intervention service form comprises at least one element requiring patient input for completion;
  - transmit, separate from the rejection response, the patient intervention service form corresponding to the at least one available intervention service for the patient to the pharmacy computer to facilitate provision of an indication of availability of the patient intervention form to a pharmacist in response to receiving a request for the prescription from the patient or an associated patient caregiver in order to permit completion of the patient intervention service form by the pharmacist; and
  - receive, a completed patient intervention service form corresponding to the transmitted patient intervention service form.

10. The system of claim 9, wherein the at least one processor is further configured to execute the computer-executable instructions to:
- determine, after receipt of the first prescription claim transaction, that the available intervention service notification associated with the at least one available intervention service has previously been transmitted to the pharmacy computer at the time prior to receiving the first prescription claim transaction;
- transmit, in response to a positive determination that the at least one available intervention service has previously been transmitted to the pharmacy computer at the time prior to receiving the first prescription claim transaction, the first prescription claim transaction to a claims processor computer of a claims processor for adjudication; and
- receive an approved adjudicated prescription claim transaction response for the first prescription claim transaction.

11. The system of claim 10, wherein the at least one processor is further configured to execute the computer-executable instructions to transmit the adjudicated prescription claim transaction response to the pharmacy computer.

12. The system of claim 9, wherein the at least one processor is further configured to execute the computer-executable instructions to:
- receive a plurality of intervention service forms comprising at least the completed patient service form;
- determine that an available intervention services reporting period has closed; and
- generate an available intervention services report comprising patient information collected from the plurality of intervention service forms.

13. The system of claim 9, wherein the at least one processor is further configured to execute the computer-executable instructions to determine that at least one service is available for the patient identified in the first prescription claim transaction comprises one or more of: (i) determining whether the product identifier identifies an eligible product, (ii) determining whether the pharmacy identifier identifies an eligible pharmacy, or (iii) determining whether a benefits provider identifier identifies an eligible claims processor.

14. The system of claim 9, wherein the at least one processor is further configured to execute the computer-executable instructions to access a patient intervention service file corresponding to the patient identifier in the first prescription claim transaction, wherein the patient intervention service file comprises one or more intervention service types available to the patient identified in the first prescription claim transaction.

15. The system of claim 9, wherein, the completed patient intervention service form comprises at least a patient signature and a date associated with the patient signature, and wherein the at least one processor is further configured to execute the computer-executable instructions to receive the completed patient intervention service form from the pharmacy computer via a facsimile.

16. The system of claim 9, wherein the at least one available intervention service for the patient is a medication therapy management service.

17. The computer-implemented method of claim 1, further comprising transmitting, by the one or more service provider computers and to a sponsor computer for a sponsor of the at least one intervention service, a notification that the at least one intervention service has been completed for the patient, wherein the notification comprises at least a portion of data in the completed patient intervention service form.

18. The system of claim 9, wherein the at least one processor is further configured to execute the computer-executable instructions to transmit, to a sponsor computer for a sponsor of the at least one intervention service, a notification that the at least one intervention service has been completed for the patient, wherein the notification comprises at least a portion of data in the completed patient intervention service form.

19. The computer-implemented method of claim 1, wherein the patient intervention service form is provided to the pharmacy computer for printing and presentation to the patient.

20. The computer-implemented method of claim 1, further comprising:

correlating the received completed patient intervention form with the previously stored patient intervention service form;

capturing and facilitating storage of data in the completed patient intervention form; and providing a notification that the patient intervention form was properly completed.

* * * * *